(12) United States Patent
Tomimatsu et al.

(10) Patent No.: US 7,301,146 B2
(45) Date of Patent: Nov. 27, 2007

(54) PROBE DRIVING METHOD, AND PROBE APPARATUS

(75) Inventors: Satoshi Tomimatsu, Kokubunji (JP); Hidemi Koike, Hitachinaka (JP); Junzo Azuma, Hitachiota (JP); Tohru Ishitani, Hitachinaka (JP); Aritoshi Sugimoto, Tokyo (JP); Yuichi Hamamura, Atlanta, GA (US); Isamu Sekihara, Fusa (JP); Akira Shimase, Yokosuka (JP)

(73) Assignees: Hitachi, Ltd., Tokyo (JP); Hitachi ULSI Systems Co., Ltd., Tokyo (JP)

( * ) Notice: Subject to any disclaimer, the term of this patent is extended or adjusted under 35 U.S.C. 154(b) by 292 days.

(21) Appl. No.: 11/201,222

(22) Filed: Aug. 11, 2005

(65) Prior Publication Data

US 2005/0269511 A1 Dec. 8, 2005

Related U.S. Application Data

(63) Continuation of application No. 10/296,887, filed on Nov. 29, 2002, now Pat. No. 6,960,765.

(51) Int. Cl.
*G01N 23/00* (2006.01)
*G21K 7/00* (2006.01)

(52) U.S. Cl. ............... 250/310; 250/307; 250/305; 250/306; 250/442.11; 250/492.21; 73/105

(58) Field of Classification Search ............... None
See application file for complete search history.

(56) References Cited

U.S. PATENT DOCUMENTS

| 4,420,686 A | 12/1983 | Onoguchi et al. ........ 250/310 |
| 5,656,812 A | 8/1997 | Takahashi .............. 250/310 |
| 6,538,254 B1 | 3/2003 | Tomimatsu et al. .... 250/442.11 |
| 6,583,413 B1 | 6/2003 | Shinada et al. ......... 250/310 |
| 6,664,552 B2 | 12/2003 | Shichi et al. ........ 250/492.21 |
| 6,717,142 B2 | 4/2004 | Hiroi et al. ........... 250/310 |

FOREIGN PATENT DOCUMENTS

| EP | 0927880 | 7/1999 |
| JP | 4150047 | 5/1992 |
| JP | 541421 | 2/1993 |
| JP | 552721 | 3/1993 |
| JP | 5114634 | 5/1993 |
| JP | 7333301 | 12/1995 |
| JP | 837211 | 2/1996 |
| JP | 9326425 | 12/1997 |
| JP | 2000147070 A | 5/2000 |
| JP | 2000171364 | 6/2000 |
| WO | 9905506 | 2/1999 |

*Primary Examiner*—Jack I. Berman
*Assistant Examiner*—Zia R. Hashmi
(74) *Attorney, Agent, or Firm*—Mattingly, Stanger, Malur & Brundidge, P.C.

(57) ABSTRACT

A probe driving method and a probe apparatus for bringing a probe into contact with the surface of a sample in a safe and efficient manner by monitoring the probe height. Information about the height of the probe from the sample surface is obtained by detecting a probe shadow (54) appearing immediately before the probe contacts the sample, or based on a change in relative positions of a probe image and a sample image that are formed as an ion beam is irradiated diagonally.

16 Claims, 18 Drawing Sheets

PROBE DRIVING METHOD, AND PROBE APPARATUS

The present application is a continuation of application Ser. No. 10/296,887, filed Nov. 29, 2002 now U.S. Pat. No. 6,960,765, the contents of which are incorporated herein by reference.

FIELD OF THE INVENTION

The present invention relates to probe apparatuses for bringing a mechanical probe into contact with the surface of a sample. For example, the invention relates to a sample preparing apparatus for preparing a microscopic device or a sample section for microscopic region analysis by separating and removing, by means of an ion beam and a probe, a microscopic sample section comprising a specific region of a sample substrate. The invention also relates to a sample diagnostic apparatus for measuring the characteristics of a sample by e.g., applying a voltage to the surface of the sample with a probe.

BACKGROUND OF THE INVENTION

JP Patent Publication (Unexamined Application) No. 5-52721: "Method of separating a sample and a method of analyzing a separated sample obtained by the separating method" (Publication 1) discloses a method of preparing a sample by separating and removing a microscopic sample section of the micrometer order with a mechanical probe. In this publication, a change in probe potential caused by the contacting of a probe to the substrate is captured as a change in luminance in a scanning ion microscopy image (to be hereafter referred to as SIM image), to judge the contact of the probe to the substrate surface.

JP Patent Publication (Unexamined Application) No. 9-326425: "Defect inspecting method and apparatus" (Publication 2) discloses a sample examining method for measuring the characteristics of a sample by bringing a mechanical probe into contact with a specific position on the sample surface and applying a voltage to the sample surface with the probe. This method will be described by referring to FIG. 26. In this method, four probes 301, 302, 303 and 304 are contacted to electrodes 305, 306, 307 and 308, respectively, on the surface of a sample. The electric characteristics among the probes are measured to determine the electric characteristics of the sample. Initially, the sample surface is scanned by a primary electron beam 309. While observing the sample surface by picking up secondary electrons 311 with a secondary electron detector 310, the probes 301, 302, 303, and 304 are moved over the electrodes 305, 306, 307, and 308. Then, the probe 301 is contacted to the electrode 305 in the following manner. When the timing immediately before the probe contacts the sample is detected ("pre-contact detection") based on the tunnel current or atomic force between the probe and sample, the movement of the probe is stopped temporarily. Thereafter, the probe is again moved closer to the electrode at a slower speed and stopped upon contact. The contact of the probe to the sample is judged by detecting a contact current with a probe current monitor, or by monitoring a change in potential of the electrode 305 with an energy filter-equipped secondary electron detector.

One of the most important things when contacting a probe to a specific region of a sample of the micrometer or sub-micrometer order is avoid damage to the probe or sample. For this reason, the contact detection techniques disclosed in Publications 1 and 2 are at least necessary. In addition, to avoid damage to both probe and sample, a means must be devised to minimize the amount of overshooting when stopping the probe. In Publication 1, it is possible to detect the timing at which the probe makes a contact, but the distance between the probe and the sample prior to contact cannot be known. For these reasons, the overall speed at which the probe approaches the sample must be reduced, which results in a longer time before contact is made. On the other hand, in Publication 2, the timing immediately before contact with the sample can be known by making the pre-contact detection. Therefore, while the speed is lowered immediately before contact, the time it takes for the probe to make contact can be reduced by setting the approach speed of the probe immediately before it makes contact at a high value.

However, the detection of tunnel current requires that the sample be electrically conductive, so that no detection can be made if the contact region is an insulator or a floating electrode. In the case of atomic force detection, the probe must be formed as a cantilever for the detection of microscopic forces, which is not easy and tends to raise costs. Furthermore, when detecting tunnel current or atomic force, the probe must be brought within nanometer-order distances of the sample before detection can be made, so a complicated and highly precise probe control apparatus capable of both coarse and fine movements is necessary. In addition, since a piezoelectric element is employed, it is difficult to maintain a single position after making contact due to creep phenomena or the like. For these reasons, a means of easily making the pre-contact detection is desired.

Further, in the above publications, while the probe's position in a plane parallel to the surface of the sample is monitored through an observed image, the distance between the probe and the sample can only be monitored in a region immediately prior to contact. To enable safe transportation of the probe, however, a technique must be devised which allows the distance between the probe and the sample to be readily determined at any desired position.

When a plurality of probes are used, they must be transported in a manner that they do not interfere with each other. However, the above-mentioned publications do not disclose any methods for transporting the probes in a plane parallel to the sample surface. Generally speaking, it is difficult to control the movement of the individual probes while monitoring their three-dimensional positional relationship. Thus, a transportation method is required by which interference among the probes can be easily removed.

Conventionally, the transportation of the probe to a position immediately above a contact target in a plane parallel to the sample surface is manually performed by monitoring an observed image. It is desired, however, to carry out this operation automatically, in order to lessen the burden on the operator. Thus, a transportation technique is required by which the coordinates of the probe tip and the contact target can be automatically detected.

Accordingly, it is a first object of the present invention to provide a probe driving method and probe apparatus by which damage to the probe and sample can be curbed by a simple probe control and by which contact can be made in a short time. A second object of the present invention is to provide a probe driving method and a probe apparatus which allows the operator to recognize the distance between the probe and the sample, allowing him to easily bring the probe into contact with the sample. A third object of the invention is to provide a probe apparatus which automatically recognizes the coordinates of the probe and sample, allowing the probe to be automatically contacted to a target position on the sample. A fourth object of the invention is to provide a sample preparation apparatus by which a removed sample can be reliably prepared without it being damaged as a result of contact with the probe. A fifth object of the invention is to provide a probe apparatus for accurately obtaining the characteristics of a sample by contacting a probe to the sample in a reliable manner.

SUMMARY OF THE INVENTION

To achieve the above objects of the invention, in one embodiment, information about the height of a probe relative to the surface of a sample is acquired by detecting the shadow of the probe created in an SIM image immediately prior to the contact of the probe to the sample. Based on that information, the drive speed and drive distance of the probe are controlled so that the probe comes into contact with the sample surface safely and efficiently. In another embodiment of the invention, the information about the height of the probe relative to the sample surface is acquired based on changes in the relative position of a probe image and a sample image appearing in a SIM image as the angle of irradiation of an ion beam is varied. Based on that information, the drive speed and drive distance of the probe are controlled so that the probe comes into contact with the sample surface safely and efficiently. Further, in another embodiment of the invention, the probe is brought into contact with the sample surface in advance and the coordinates of the probe tip at that time (position information about the height of the probe as it contacts the sample surface) are measured and stored. The stored information is compared with the current height of the probe when it is located above the sample to thereby acquire accurate probe height information, based on which the probe's drive speed and drive distance are controlled such that it comes into contact with the sample surface safely and efficiently.

Specifically, a probe driving method according to one embodiment of the invention comprises two steps. In the first step, a sample and probe are irradiated with a beam of charged particles. Secondary particles or reflected particles emitted by the irradiation of the charged particle beam are detected to produce a sample image including an image of the probe. The probe is transported toward the sample at a first speed while the sample image is monitored. In the second step, the drive speed of the probe is switched from the first speed to a slower second speed upon detection of a reduction in luminance in a region adjacent to the probe image in the sample image. This method allows the probe to be detected immediately prior to contact with the sample even over a floating electrode or the like.

A probe driving method according to another embodiment of the invention comprises four steps. In the first step, a sample and a probe are irradiated with a beam of charged particles at a first angle. Secondary particles or reflected particles emitted by the irradiation of the charged particle beam are detected to produce a sample image including an image of the probe, and the distance (a first distance) between the position of the probe tip and a specified position on the sample is determined. In the second step, the sample and the probe are irradiated with a beam of charged particles at a second angle, which is different from the first angle. Secondary particles or reflected particles emitted by the irradiation of charged-particle beam are detected to produce a sample image including an image of the probe. Then the distance (a second distance) between the positions of the probe tip and the above-mentioned specified position on the sample is determined on the sample image. In the third step, the distance between the sample and the probe is calculated based on the first and second angles and the first and second distances. In the fourth step, the probe is driven toward the sample in accordance with the calculated distance between the sample and the probe.

A probe driving method according to another embodiment of the invention comprises three steps. In the first step, the coordinates of the tip of a probe, when it is in contact with the sample, in a direction intersecting the sample surface are measured and recorded by a measurement means. In the second step, the current distance between the probe and the sample is determined based on the recorded probe tip coordinates and the current probe tip coordinates measured by the measurement means. In the third step, the probe is brought into contact with the sample while controlling the probe drive distance and drive speed in accordance with the determined distance.

A probe apparatus according to another embodiment of the invention comprises; a movable sample base on which a sample is to be placed; a charged particle optical system for irradiating the sample with a beam of charged particles; a detector for detecting secondary particles or reflected particles emitted or reflected by the sample as it is irradiated with the beam of charged particles; a probe to be mechanically contacted to the sample surface; a probe control apparatus for controlling the driving of the probe, a display apparatus for displaying the information detected by the detector in the form of an image; and a detection information analyzing apparatus for analyzing the information detected by the detector. The probe control apparatus controls the probe driving apparatus based on the result of analysis by the detection information analyzing apparatus.

The detection information analyzing apparatus may comprise a function for detecting a change in luminance in a region adjacent to the probe in the image.

When the detection information analyzing apparatus detects a reduction in luminance in a region adjacent to the probe while the probe is being transported toward the sample at the first speed, the probe control apparatus switches the drive speed of the probe moving toward the sample from the first speed to a slower, second speed.

When the detection information analyzing apparatus detects a reduction in luminance in a region adjacent to the probe while the probe is being transported toward the sample at the first speed, the probe control apparatus switches the drive speed of the probe moving toward the sample from the first speed to the slower, second speed. When the detection information analyzing apparatus detects a sudden increase in luminance in the region adjacent to the probe while the probe is being transported toward the sample at the second speed, the probe control apparatus terminates the driving of the probe.

The detection information analyzing apparatus may comprise a function for calculating the distance between the probe and the sample based on the coordinates of the tip position of the probe and the specific position on the sample in a plurality of images obtained by irradiating the probe and the sample surface with the charged particle beam at different angles.

The probe apparatus may comprise a probe for transferring a separated and removed part of a sample to another member, and a sample holder retaining tool for retaining a sample holder that holds the removed sample.

The display apparatus may display information relating to the distance between the sample surface and the probe.

A probe apparatus according to another embodiment of the invention comprises: a movable sample base for mounting a sample; a charged particle optical system for irradiating the sample with a beam of charged particles; a detector for detecting secondary particles or reflected particles emitted or reflected by the sample as it is irradiated with the charged particle beam; a display apparatus for displaying the information acquired by the detector in the form of an image; a probe to be mechanically brought into contact with the sample surface; a probe control apparatus for controlling the driving of the probe; and a probe reference coordinates recording apparatus for recording the coordinates of the probe tip which are obtained by contacting the probe to the sample in advance. The probe control apparatus controls the drive distance and speed of the probe based on the coordinates recorded in the probe reference coordinates recording apparatus and the coordinates of a position of the sample where the probe is to be brought into contact with the sample.

A probe apparatus according to another embodiment of the invention comprises a movable sample base for mounting a sample; a charged particle optical system for irradiating the sample with a beam of charged particles; a detector for detecting secondary particles or reflected particles emitted or reflected from the sample as it is irradiated with the charged particle beam; a display apparatus for displaying the information detected by the detector in the form of an image; a plurality of probes to be mechanically brought into contact with the sample surface; and a probe control apparatus for transporting the probes parallel to the sample surface such that the individual probes are transported within the individually different, specific distances until they reach the sample surface.

In the case where there are provided a plurality of probes and a probe electric control apparatus for performing electric control such as the application of a voltage to the probe or the measuring of the electric characteristics of the sample, the probe electric control apparatus may comprise an inter-probe, electrically controlled switching apparatus for switching between electric control of any desired probe and electric control of any other desired probes. In this way, probe symmetry can be ensured and thus probe control can be facilitated.

BEST MODE FOR CARRYING OUT THE INVENTION

The invention will be hereafter described in detail by referring to the attached drawings.

EMBODIMENT 1

Figure 1:
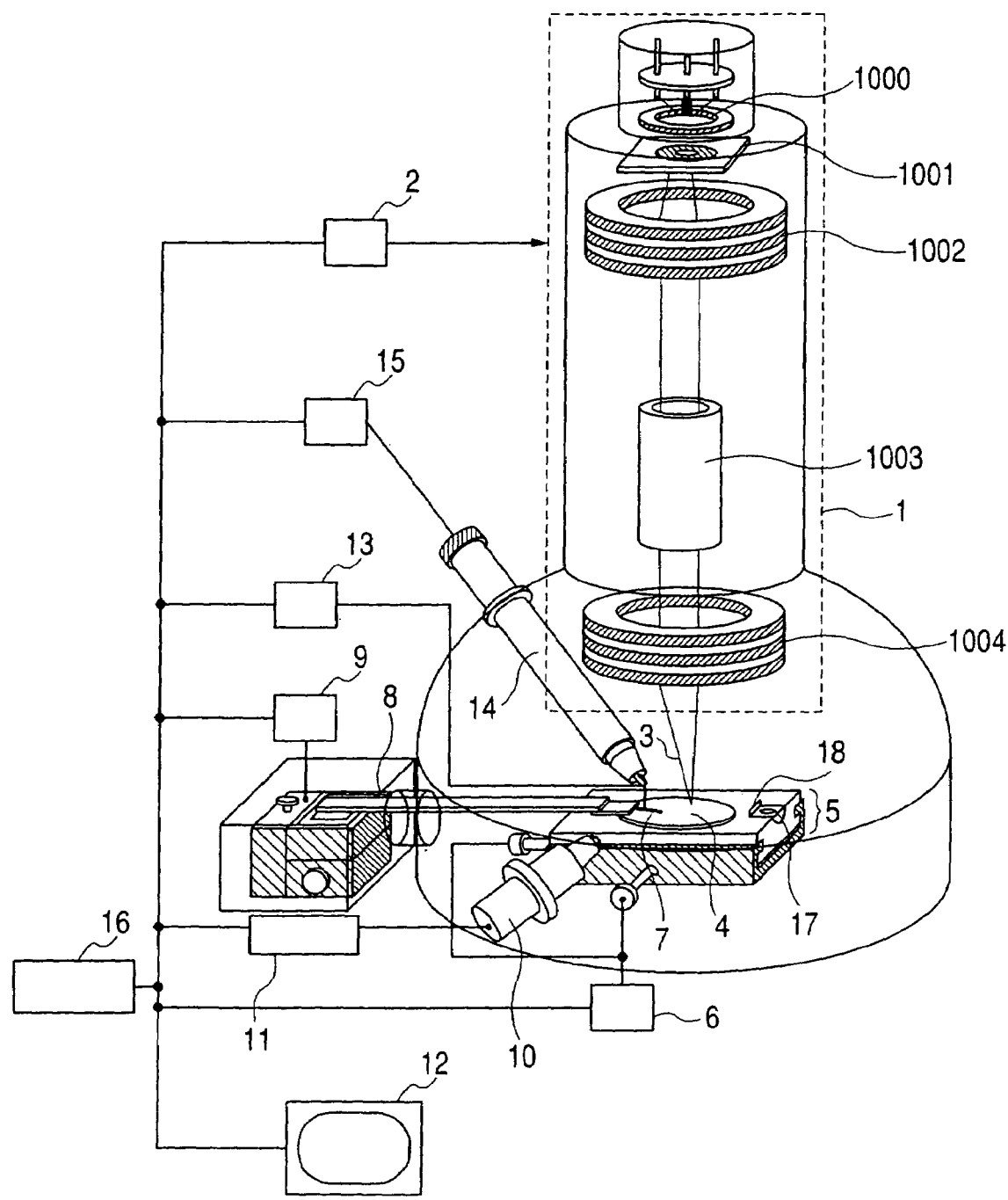
FIG. 1 is a block diagram of an example of a sample preparation apparatus according to the invention.

FIG. 1 shows a block diagram of an embodiment of the sample preparation apparatus according to the present invention for preparing a microscopic analysis sample or a microscopic device by a focused ion beam (FIB).

A sample 4 to be analyzed, such as a semiconductor wafer or chip, is mounted on a movable sample base 5 and positioned by a sample base control apparatus 6. The sample base control apparatus 6 controls the position of the sample base 5 for determining the diagnosis position of the sample 4. A removed sample holder 18 for mounting a removed sample is fixed by a removed sample holder retainer 17 on the sample base 5. A probe 7 detects device characteristics such as the resistance and current in the sample 4 as well as supplying voltage thereto, under the control of a probe electric control apparatus 13. The probe 7 is driven by a probe driving apparatus 8 which is controlled by a probe control apparatus 9.

An ion beam optical system 1 for irradiating the sample 4 with a beam of ions emitted by an ion source 1000 comprises: a beam limiting aperture 1001 for limiting the ion beam emitted by the ion source to a predetermined size; a focusing lens 1002 for focusing the ion beam; a deflector 1003 for deflecting the ion beam to a predetermined position on the sample; and an objective lens 1004 disposed in front of the sample for irradiating the sample with a deflected beam. The ion beam optical system 1 is controlled by an ion beam control apparatus 2. Secondary electrons generated when the sample or the probe is irradiated by the ion beam 3 from the ion beam optical system 1 are detected by a secondary electron detector 10. The thus detected secondary electrons are input to a display apparatus 12 as a luminance signal in synchronism with a scan signal applied to the deflector 1003, whereby an image of the sample surface and/or the image of the probe 7 are displayed on the display apparatus 12. In this process, the probe control apparatus 9 is controlled by a secondary electron information analyzing apparatus 11 identifying a certain portion of the secondary electron information, as will be described in detail later. A deposition gas source 14 is controlled by a deposition gas source control apparatus 15. It supplies tungsten carbonyl gas, for example, above the sample 4, where the ion beam 3 is irradiated to form a tungsten film on the irradiated portion, thereby forming a protective film, bonding the probe 7 and the removed sample, or bonding the removed sample and the removed sample holder 18.

The ion beam control apparatus 2, deposition gas source control apparatus 15, probe electric control apparatus 13, probe control apparatus 9, secondary electron information analyzing apparatus 11, sample base control apparatus 6, and display apparatus 12 are controlled by a calculation processing unit 16. The calculation processing unit 16 may be realized in a personal computer or a workstation comprising the ion beam control apparatus 2, deposition gas source control apparatus 15, probe electric control apparatus 13, probe control apparatus 9, secondary electron information analyzing apparatus 11, and sample base control apparatus 6.

Figure 2:
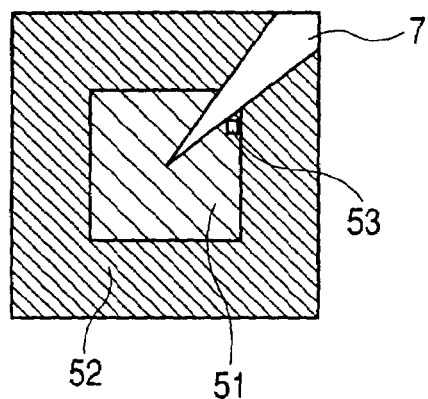
FIG. 2 shows a SIM image at the time when a probe is away from the sample surface.
Figure 3:
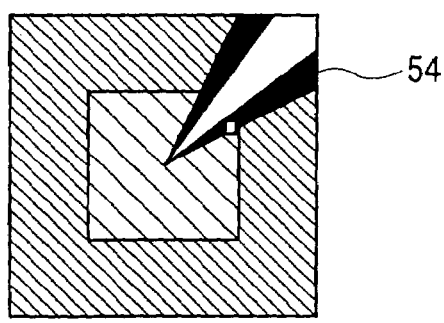
FIG. 3 shows a SIM image at the time when the probe is close to the sample surface.
Figure 4:
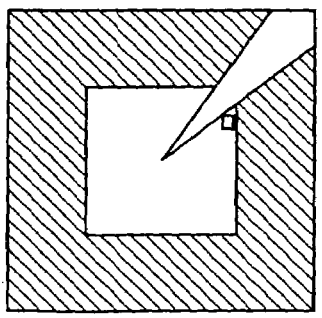
FIG. 4 shows a SIM image at the time when the probe is in contact with the sample surface.

The method of driving the probe will be described by referring to FIGS. 2-5. The approach and contact of the probe to the sample surface is explained. FIGS. 2-4 each show a secondary electron image displayed on the display apparatus 12. Numeral 51 designates a pad with which the probe 7 is to be brought into contact. Numeral 52 designates an insulating region. Usually, the distance between the probe 7 and the sample 4 cannot be directly determined based on the observed image displayed on the display apparatus 12. In order to curb damage to both the probe 7 and the surface of the sample 4 as the former contacts the latter, the speed at which the probe 7 approaches the sample surface should desirably be reduced. This means, however, that, when the distance between the probe and the sample is unknown, the probe approach speed has to be reduced throughout the entire distance of probe transportation, thereby requiring a long time before the probe contact operation can be completed. If the pre-contact detection can be made, the probe speed can be controlled in accordance with its distance from the sample surface, such that contact can be made in a short time without damage. In the present embodiment of the invention, a shadow 54 of the probe 7 is utilized for the pre-contact detection.

In the present embodiment, a secondary electron signal produced by a positive ion FIB irradiation is shown on the display apparatus 12 as an image. At this time, the probe itself is connected to the probe electric control apparatus 13, so that the probe is not charged even when irradiated with the FIB. However, when the contact pad 51 is electrically floating, the pad 51 is positively charged. This is because the ingress of positive ions and the emission of the negative secondary electrons constitute the dominant process. As a result, in a region where the probe 7 is sufficiently away from the sample surface, the secondary electrons emitted by the sample by the FIB irradiation are drawn back to the sample before they arrive at the secondary electron detector, so that the secondary electron signal, i.e., the luminance in the display apparatus 12 appears dark, as shown in FIG. 2.

Figure 6:
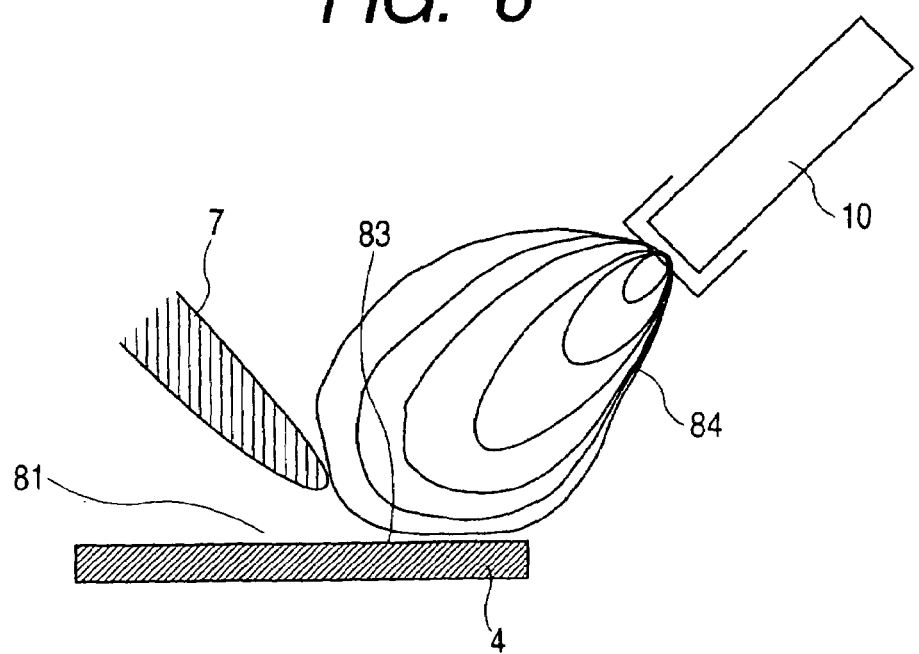
FIG. 6 illustrates an electric field for inducing secondary electrons in a plane perpendicular to the sample surface.
Figure 7:
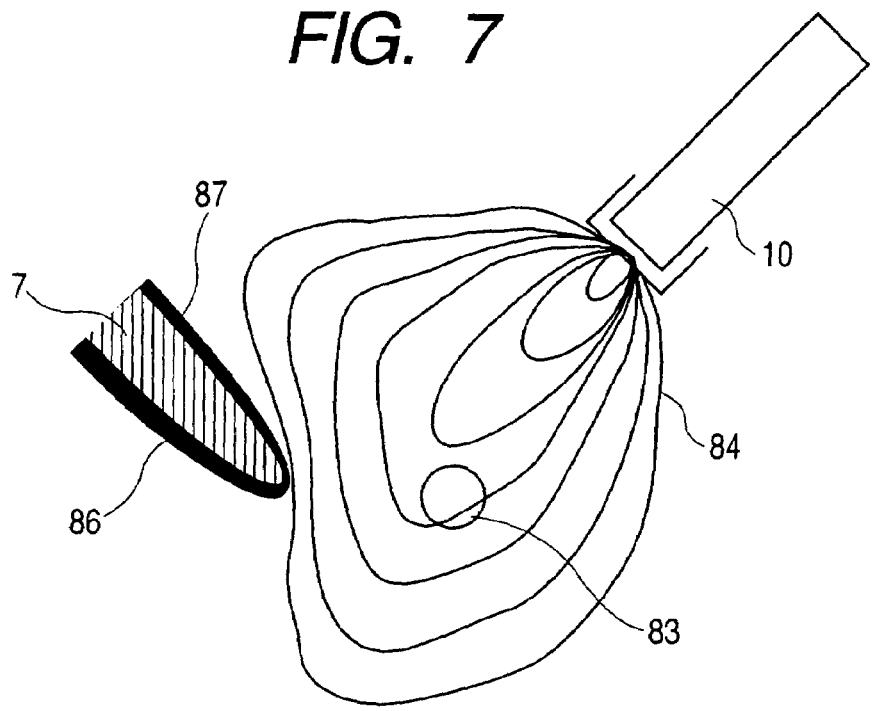
FIG. 7 illustrates an electric field for inducing secondary electrons in a plane parallel to the sample surface.

As the probe 7 approaches the sample surface, the probe increasingly blocks the arrival of the secondary electrons emitted by the sample surface near the probe at the secondary electron detector 10. Thus, the shadow 54 is observed, as shown in FIG. 3. Specifically, the shadow 54 is observed for the following reasons. FIG. 6 schematically shows the induction electric field of the secondary electron detector 10 in the presence of the probe 7, as seen from a direction parallel to the surface of the sample 4. The secondary electrons generated by ion beam irradiation at a position 83 on the sample surface away from the probe 7 are drawn into the secondary electron detector 10 by its induction electric field indicated by an equipotential surface 84. But secondary electrons generated at a position 81 on the sample surface below the probe 7 are not easily drawn into the secondary electron detector 10 because the induction electric field of the secondary detector 10 is blocked by the probe 7. As a result, the SIM image appears dark. FIG. 7 schematically shows the electric field as the probe 7 approaches the sample surface, as seen from a direction perpendicular to the sample surface. Electrons generated at a position 83 on the sample surface away from the probe 7 are accelerated by the induction electric field of the secondary electron detector 10 indicated by the equipotential surface 84, and fed into the secondary electron detector. If the probe 7 is near the sample surface, however, the induction electric field 84 cannot easily expand near the probe. Thus, secondary electrons generated at regions 86 and 87 on the sample surface near the probe are not readily accelerated toward the secondary electron detector 10 and are therefore not detected by the secondary electron detector 10, resulting in a dark shadow on the secondary electron image. The shadow 54 of FIG. 3 appears when, for example, the approaching probe 7 is about 20 μm from the surface of the sample.

Figure 5:
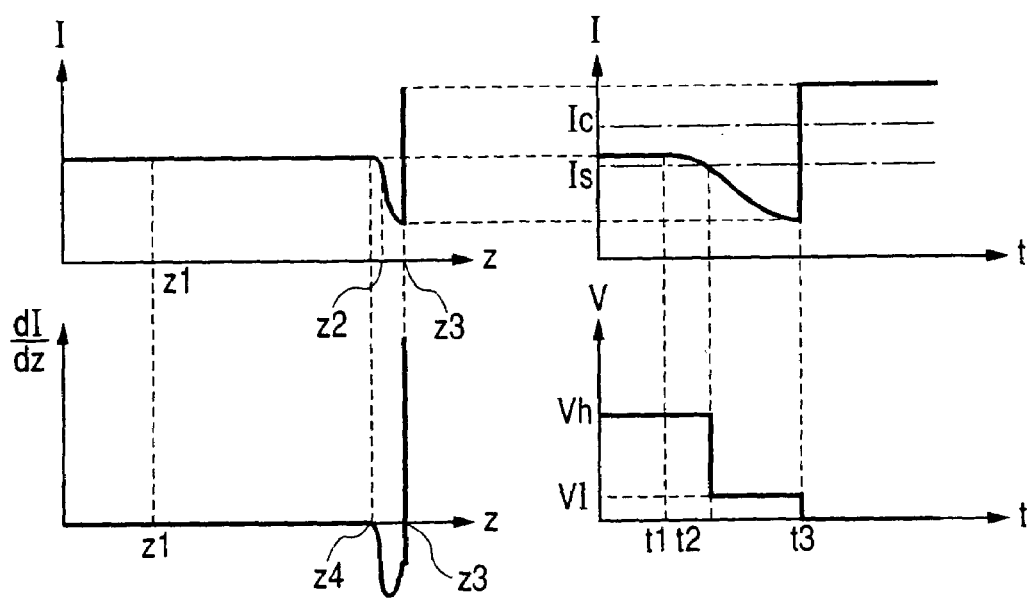
FIG. 5 shows the relationship among luminance in a monitored region, probe-to-sample distance, elapsed time, and a probe's approaching speed.

As the probe 7 further approaches the sample and contacts the pad 51, the charge on the pad 51 is relaxed by the electrons injected by the probe 7, thereby increasing the luminance of the pad 51 on the observed image, as shown in FIG. 4. The upper-left part of FIG. 5 shows a change in luminance monitored in a luminance monitored region 53 designated by a mouse, for example, on the display apparatus 12, as shown in FIG. 2. In FIG. 5, the horizontal axis indicates the z-transportation distance of the probe, while the vertical axis indicates the luminance of the luminance monitored region 53. Position z1 corresponds to the position of the probe in a region, as in FIG. 2, where the probe is sufficiently distanced away from the sample. Position z2 corresponds to the position of the probe in a region where a shadow is observed as shown in FIG. 3. Position z3 is the sample surface position corresponding to FIG. 4. The distances are, for example, about 500 μm between positions z3 and z1, and about 10 μm between positions z3 and z2. At position z3, the probe 7 contacts the sample such that the charge on the contact pad 51 is relaxed, resulting in a sudden increase in luminance in the observed image.

If a voltage which is positive relative to that of the sample 4 is applied to the probe 7 by the probe electric control apparatus 13, the probe 7 draws secondary electrons such that the field of view is darkened overall, making it difficult to identify the shadow 54 of the probe. Conversely, if a voltage negative relative to that of the sample 4 is applied to the probe 7, the probe 7 can be observed more brightly and so the shadow 54 can be more easily identified.

By utilizing the above phenomena, the probe can be efficiently contacted in a flow as shown in the lower-right portion of FIG. 5, in which the horizontal axis indicates the time since the start of approach of the probe to the sample. Against the time axis, the relationship between changes in luminance I in the luminance monitored region 53 and the set probe approach speed v is shown. In an initial region where the luminance I is such that Is<I<Ic, the probe is brought closer to the sample with an approach speed v set at a high speed (vh). As the luminance I in the luminance monitored region 53 starts to drop (t1), and when I<Is (t2), the probe approach speed v is changed to a low speed (v1). Upon contact, the luminance I increases and when I>Ic, the probe is stopped by setting its approach speed v at zero (t3). Is and Ic are set with respect to luminance I (Z1), that is the luminance in a region Z1 where the probe is sufficiently away from the sample surface, such that Is=0.8×I(Z1) and Ic=2×I(Z1). Through the above-described flow, the probe can be brought into contact with the sample in a short time without damaging either. When there is not enough luminance change in the luminance monitored region 53, the luminance I can be differentiated with respect to distance as shown in the lower-left part of FIG. 5, thereby emphasizing the variation and facilitating the acquisition of positional information. Displaying a distance-differentiated graph of the luminance I on the display apparatus 12 helps the operator identify the probe position.

The above example assumed the presence of the contact pad 51 for ease of explanation. However, the shadow 54 of the probe is observed in the absence of the contact pad, so that the timing immediately before the probe makes contact can be monitored. Namely, in this flow, the pre-contact detection can be made even when the sample under investigation is an insulator. Furthermore, this system is capable of making the pre-contact detection at a stage when the distance between the probe and the sample surface is greater than that at which the pre-contact detection is made in the tunnel current detection system or atomic force detection system. Thus, the required level of probe braking accuracy is not so high. Accordingly, this system allows a probe driving apparatus or probe control apparatus to be manufactured inexpensively.

In the case where the sample is electrically conductive, the probe can be safely contacted with the sample through the following flow. First, a bias voltage is applied to the probe 7 via a high resistance. When the probe 7 is far away from the sample 4, the luminance monitored region near the probe is not influenced by the probe 7 and exhibits the secondary electron luminance of the sample itself. As the probe 7 approaches the sample 4, the luminance of the luminance monitored region near the probe decreases, due to the inability of the secondary electron induction electric field of the secondary electron detector 10 to expand near the probe, as described with reference to FIGS. 6 and 7. Then the probe approach speed is lowered. The probe 7 further approaches the sample 4 and eventually comes into contact with the sample 4, whereupon the potential of the probe 7 drops to that of the sample via the high resistance. As a result, the blocking of the second electron induction electric field is relaxed and the sample luminance near the probe is brought back to normal. By detecting this, the contact of the probe 7 to the sample 4 can be determined, whereupon the driving of the probe is terminated. Thus, in the case of a conductive sample as well, the probe can be brought into contact with the sample in an efficient manner by the apparatus according to the present invention.

Figure 8:
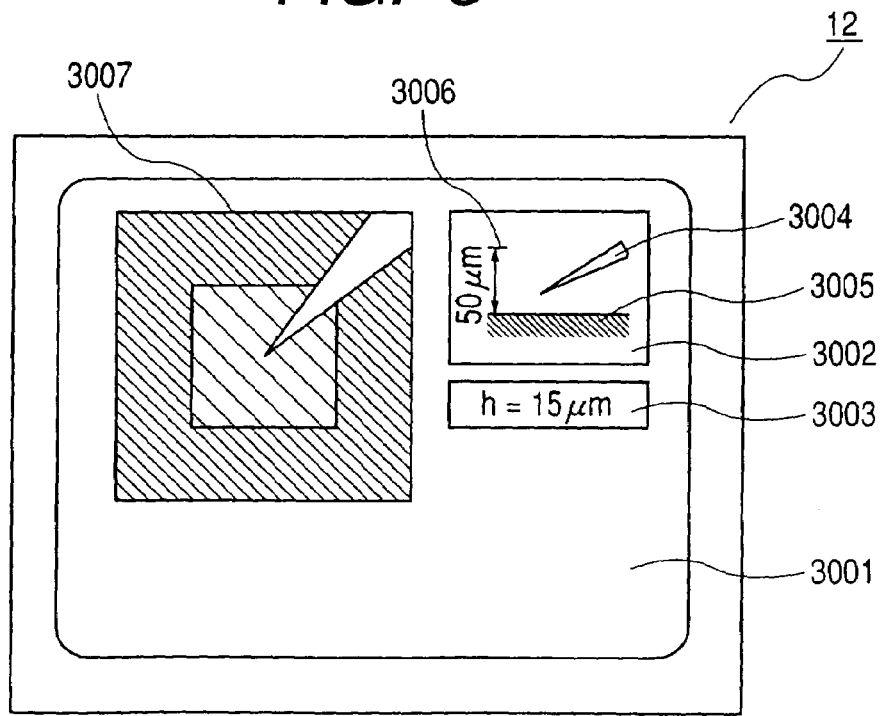
FIG. 8 shows an example of the display of probe height on a display apparatus in the apparatus according to the invention.

Because the change in the luminance I in the luminance monitored region 53 can be related to the distance between the probe 7 and the sample, the information about the height of the probe above the sample surface can be displayed on the display apparatus 12, as shown in FIG. 8. Specifically, a display screen 3001 can include an SIM image display portion 3007, a probe height display portion 3002, and a probe-to-sample distance display portion 3003 as subordinate screens. In the probe height display portion 3002, a sign 3005 indicating the sample surface, a sign 3004 indicating the probe, and a size display bar 3006 indicating the size are displayed. A specific value of the probe height is indicated in the probe-to-sample distance display portion 3003. These screens allow the operator to recognize the distance between the probe and the sample intuitively.

Figure 9:
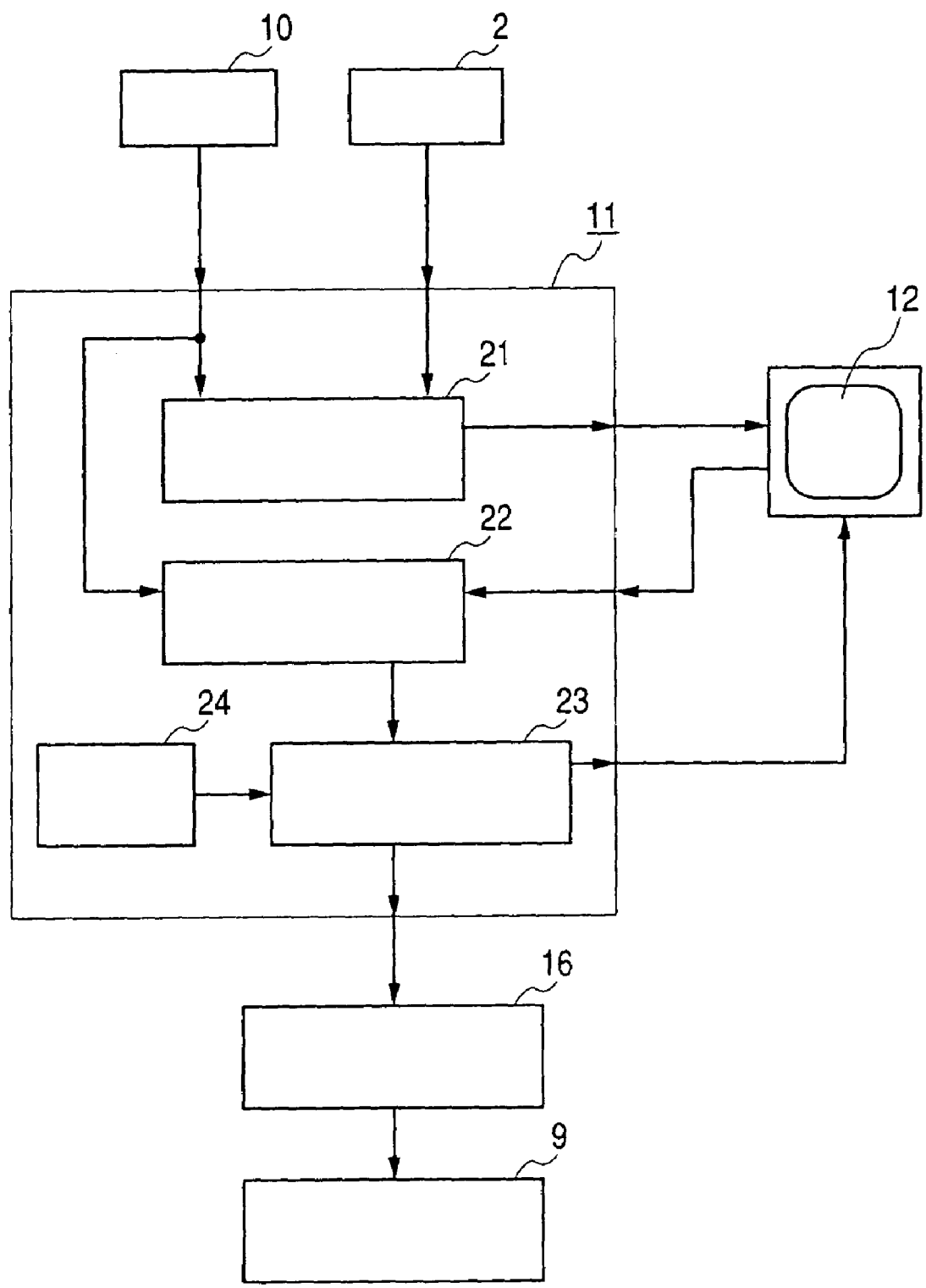
FIG. 9 schematically shows an example of a secondary electron information analyzing apparatus according to the invention.

FIG. 9 is a drawing for the explanation of the flow of signal transmission and reception involving the secondary electron information analyzing apparatus 11. An image is generated in an SIM image generating unit 21 based on the deflector scan signal from the ion beam control apparatus 2 and the secondary electron luminance information from the secondary electron detector 10, and is displayed on the display unit 12. By designating a luminance monitored region 53 (see FIGS. 2-4) by means of a pointing device such as a mouse, the coordinates of the luminance monitored position are set in a monitored portion luminance accumulating unit 22, where a luminance signal corresponding to the coordinate region is accumulated. The accumulated luminance information is compared in a luminance comparison unit 23 with a comparative luminance (such as Is and Ic in FIG. 5) which is set in advance in a comparative luminance information unit 24. As a result, the height information is obtained, and an appropriate approach speed is set in a calculation processing unit 16. Based on the resultant signal, the probe control apparatus 9 controls the driving of the probe 7, as described with reference to FIG. 5. The height information from the luminance comparison unit 23 is displayed on the display apparatus 12. In this manner, efficient probe control can be effected.

Figure 10:
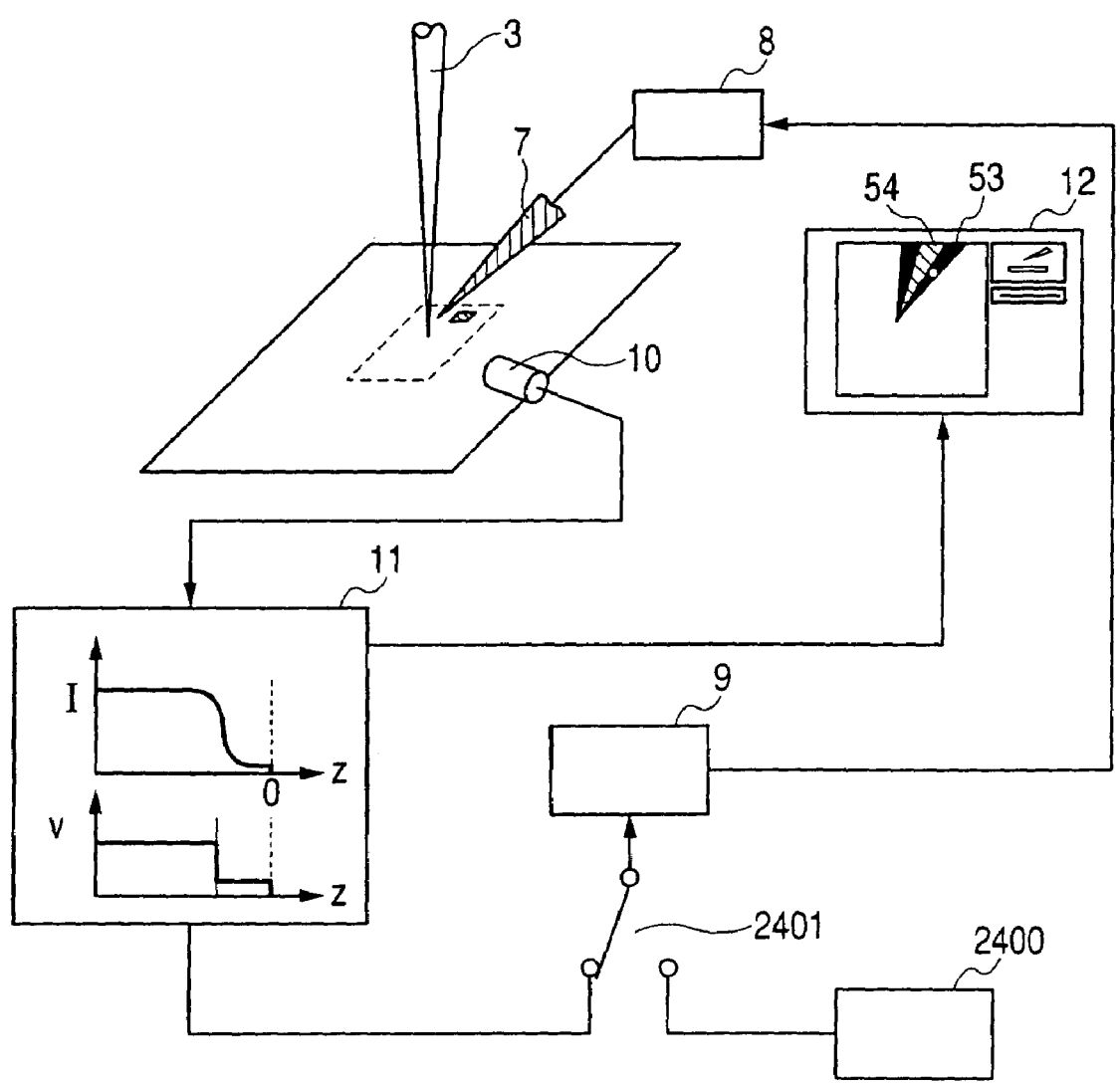
FIG. 10 illustrates the concept of probe control in the apparatus according to the invention.

FIG. 10 visually illustrates the overall flow of the signal. The secondary electrons generated as FIB 3 scans are fed into the secondary electron detector 10. The luminance of the luminance monitored region 53 is analyzed by the secondary electron information analyzing apparatus 11, and the distance between probe and sample is calculated based on the resultant luminance information and displayed on the display apparatus 12. The secondary electron information analyzing apparatus 11 further calculates an appropriate probe drive speed suitable for the probe-to-sample distance, and gives a speed instruction to the probe control apparatus 9. In response, the probe control apparatus 9 controls the probe driving apparatus 8, by which the probe 7 is driven, such that the probe is brought into contact with the sample in an efficient and safe manner. At this time, the change-over switch 2401 is connected to the secondary electron information analyzing apparatus 11. When the probe approach is to be made manually, the change-over switch 2401 is connected to a probe operating apparatus 2400. The probe operating apparatus 2400 comprises an input device such as a push button, joystick, mouse, or the like. When the probe operating apparatus 2400 is selected by the change-over switch 2401, the probe is operated manually by the operator viewing the probe height information in the display apparatus 12. The manual operation can be facilitated by providing a function, through an indicator or a buzzer, for example, for notifying the operator of a luminance or a change in luminance detected by the secondary electron information analyzing apparatus 11 at which the speed should be changed.

Figure 11:
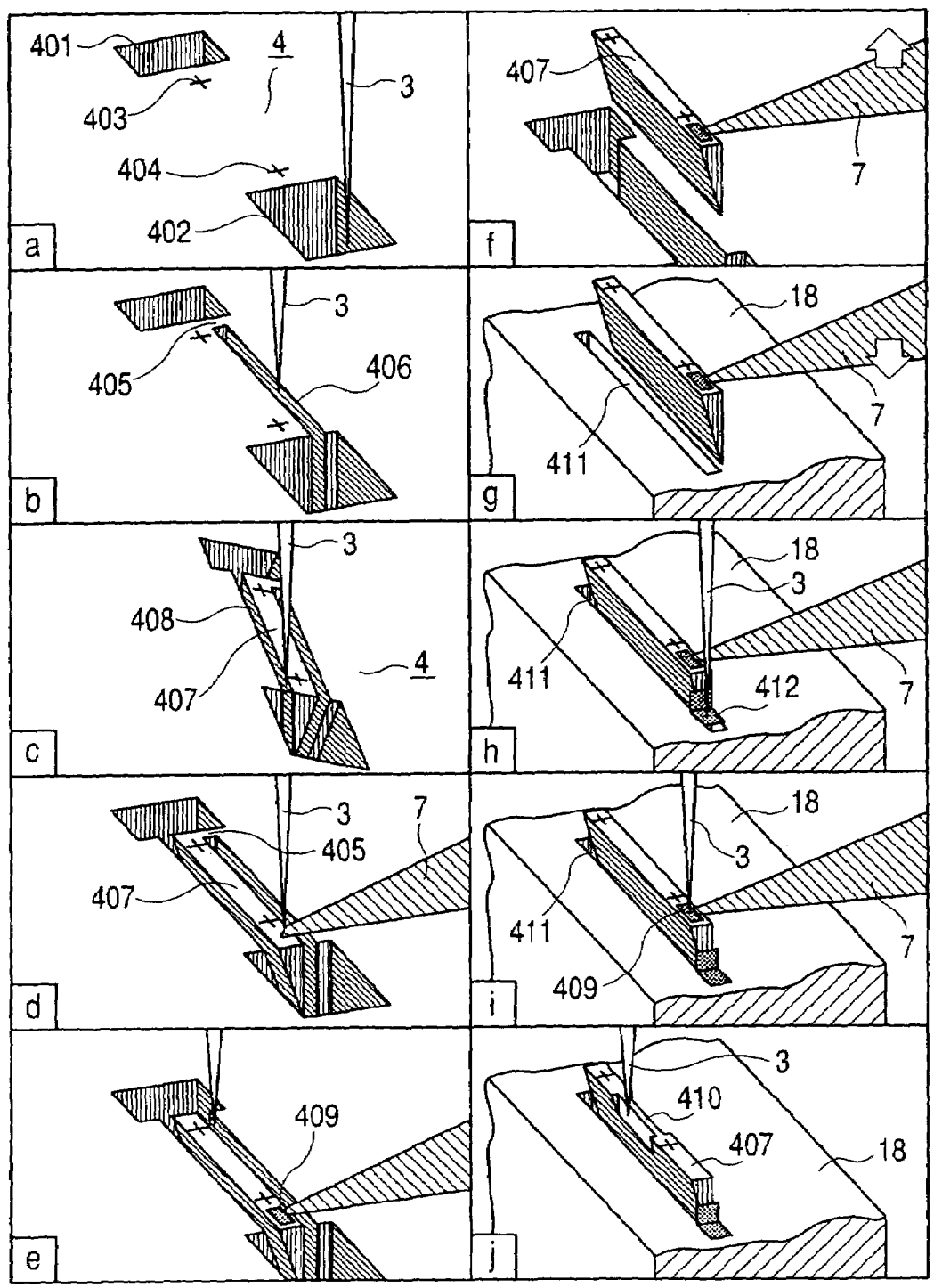
FIG. 11 illustrates the individual steps of the process of preparing a removed sample by means of the apparatus according to the invention.

FIG. 11 illustrates a method of preparing a sample using the above-described apparatus according to an embodiment of the invention.

Initially, marks 403 and 404 for identifying the target position are formed by irradiation by a FIB 3. Rectangular openings 401 and 402 are then formed in a sample 4 outside either opening (FIG. 11(*a*)). Then, a rectangular groove 406 is formed by FIB 3, leaving a support portion 405 (FIG. 11(*b*)). Thereafter, the sample base 5 is tilted so that the sample surface can be irradiated with FIB 3 diagonally to thereby form an angled groove 408. As a result, a removed sample 407 connected with the sample 4 only via the partial support portion 405 is formed (FIG. 11(*c*)). The sample base is then brought back to the original angle, and the probe driving apparatus 8 is controlled by the probe control apparatus 9 such that the probe 7 is brought into contact with a part of the removed sample 407 through the probe driving flow described with reference to FIG. 5. While the support portion 405 of the removed sample is later cut by FIB, the cutting should desirably be done in a short time in light of the possibility of probe drift, for example. Therefore, the volume of the support portion should be minimized. This, however, gives rise to the fear that the support portion 405 might be damaged by contact with the probe 7. Thus, the probe is brought into contact by the above-described probe control method in order to minimize damage. The contacting probe 7 and the removed sample 407 are immobilized by means of an IBAD film 409 (FIG. 11(*d*)). Then, the support portion 405 is cut by FIB 3 (FIG. 11(*e*)).

The removed sample 407 is thus cut from the sample 4 and removed as the probe 7 is raised by the probe driving apparatus 8 (FIG. 11(*f*)). The thus removed sample 407 is contacted to a groove 411 formed in a removed sample holder 18 (FIG. 11(*g*)). This contact should be made with a sufficiently small speed lest the removed sample 407 be damaged or detached at IBAD film portion 409 and thus lost. Thus, the above-described contact method is required. When the removed sample is brought closer to the removed sample holder, a shadow of the removed sample corresponding to the shadow 54 of the probe described by referring to FIG. 3 appears. For this reason, the height of the removed sample can be recognized by monitoring the luminance near the removed sample, so that the probe approach speed can be controlled as shown in FIG. 5. After making contact, the probe and the sample are immobilized by means of an IBAD film 412 (FIG. 11(*h*)). After immobilization, the probe-connected portion is irradiated with FIB, sputtering takes place, and the probe is separated from the removed sample 407 (FIG. 11(*i*)). When the removed sample 407 is to be used as a TEM sample, the sample is again irradiated with FIB 3, and an observation region 410 is processed to a thickness of 100 nm or less in a finishing process (FIG. 11(*j*)). When the sample is to be used for preparing a sample for other analysis or measurement purposes, the process of thinning the observed region is not necessarily required.

This technique can be applied not only to the preparation of an analysis sample but also to the preparation of a device. For example, a unit cell may be removed from a sample substrate on which device unit cells are prepared, using the same flow as for the removal of the removed sample 407. The removed unit cell may be transplanted to a part of another device to create a new device. Since in this case the microscopic unit cell must be removed, transported and fixed without being damaged, the above-described probe driving method, which is capable of making the pre-contact detection, can be effectively used.

Figure 12:
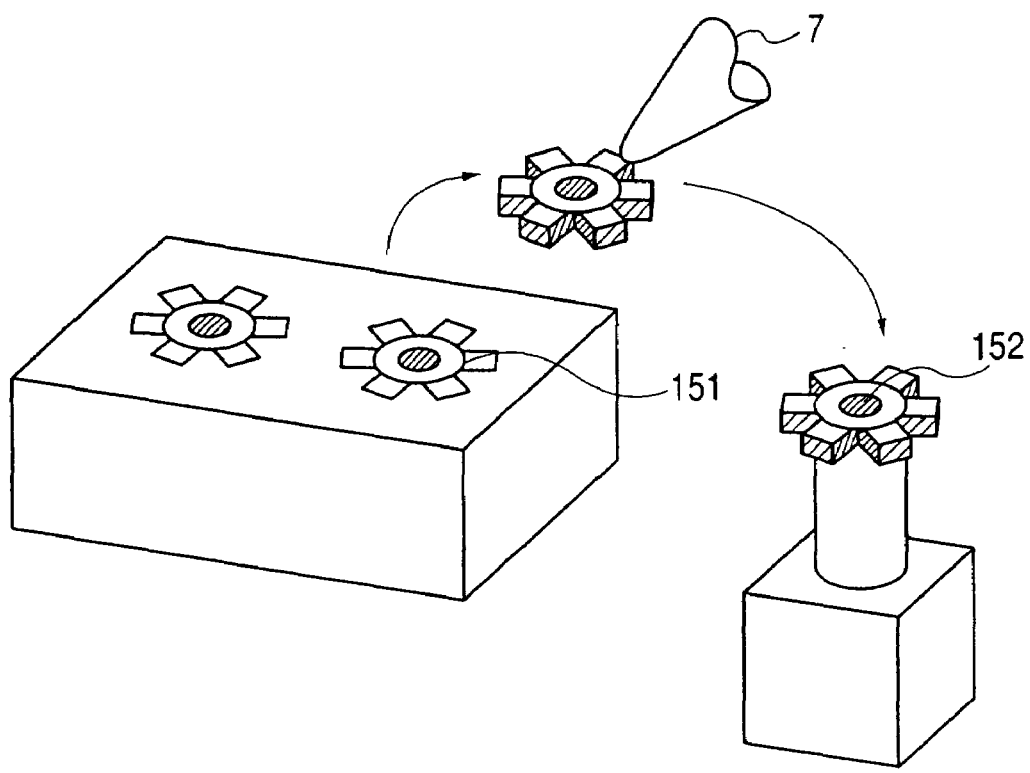
FIG. 12 illustrates an example of the manner in which parts are assembled for preparing a microscopic machine according to the invention.

The technique can also be applied to the manufacture of microscopic machines. For example, as shown in FIG. 12, a gear part 151 of a microscopic machine of the order of microns formed on a substrate by FIB processing or lithography may be removed by the above-described removal flow and inserted into a bearing 152. Thus a microscopic component can be assembled and a microscopic machine can be produced. In the manufacture of such a machine, the microscopic gear part 151 and the bearing 152 must be removed, transported and fixed without damage. Thus, the above-described probe driving method can be effectively used.

EMBODIMENT 2

The process of monitoring the probe-to-sample distance will be described by referring to FIGS. 13-16. While the pre-contact detection technique was described in Embodiment 1, in the present embodiment, the method of identifying the current distance between the probe and the sample will be described.

Figure 13:
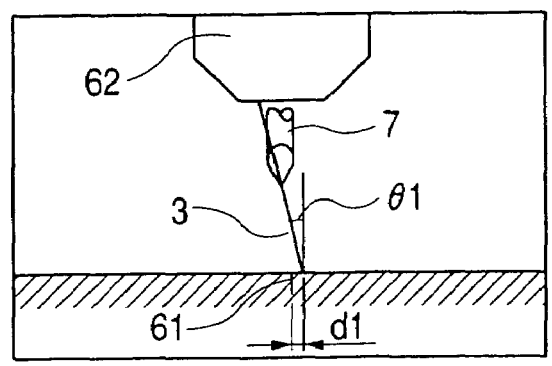
FIG. 13 shows the positional relationship between the probe and the sample in the case of FIBθ1 diagonal irradiation according to the invention.
Figure 14:
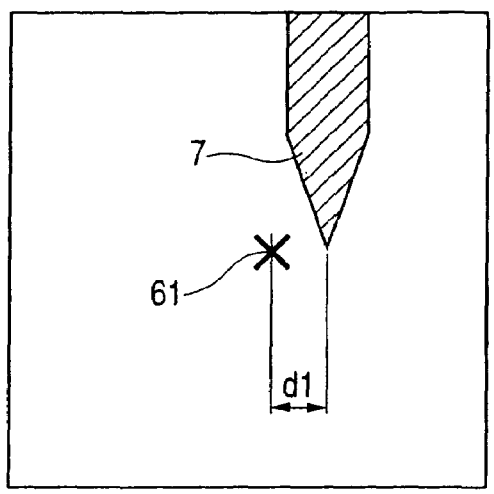
FIG. 14 shows a SIM image in the case of FIBθ1 diagonal irradiation according to the invention.
Figure 15:
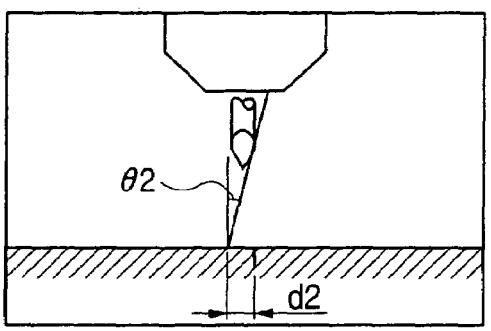
FIG. 15 shows the positional relationship between the probe and the sample in the case of FIBθ2 diagonal irradiation according to the invention.
Figure 16:
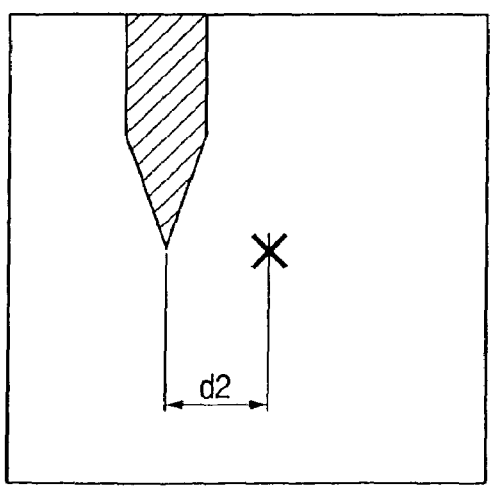
FIG. 16 shows a SIM image in the case of FIBθ2 diagonal irradiation according to the invention.

FIG. 13 schematically shows the relationship among an ion emitting portion 62 of the FIB optical system, a probe 7 and a sample 4. FIG. 14 shows an observed image displayed on a display apparatus 12. Numeral 61 designates a specific position on the surface of the sample that is indicated by a marking produced by FIB processing. The position, however, may be indicated by a structural feature on the sample. When the probe 7 and the sample 4 are irradiated with the FIB in an inclined manner such that the angle formed by the beam and the optical axis of the system is θ1, the distance between the tip of the probe 7 and the marking 61 is observed as d1 in the observed SIM image, as shown in FIG. 14. When the FIB is inclined to the side opposite to the case of FIG. 13 with an angle θ2, as shown in FIG. 15, the distance between the tip of the probe and the marking 61 is observed as d2 on the opposite side in the observed SIM image, as shown in FIG. 16. Based on these two observation results, the distance h between probe and sample can be expressed by the following equation:

$$h = (d1 + d2) \cdot \cos\theta 1 \cdot \cos\theta 2 / \sin(\theta 1 + \theta 2) \quad (1)$$

When the FIB angles θ1 and θ2 are both equal to θ, equation (1) can be simplified to:

$$h = (d1 + d2)/(2 \cdot \tan\theta) \quad (2)$$

The relationship between the deflection voltage V and the FIB angle θ can be obtained as follows. A deflection constant Cd prescribed by the apparatus is defined as follows:

$$Cd = dV/dx \quad (3)$$

where x is the deflection amount.

When the distance between a deflection center and the sample surface is assumed to be Lw, $$Lw \cdot \tan\theta = x \quad (4)$$

so that, when the deflection voltages corresponding to the angles θ1 and θ2 are V1 and V2, respectively, $$\theta 1 = \arctan(V1/(Lw \cdot Cd)) \quad (5)$$

$$\theta 2 = \arctan(V2/(Lw \cdot Cd)) \quad (6)$$

Thus, the distance h between probe and sample can be determined based on V1, V2, d1 and d2. When V1=V2=V (θ1=θ2=θ), $$h = (d1+d2) \cdot Lw \cdot Cd/(2V) \quad (7)$$

Thus, by measuring the distances d1 and d2 during deflection by the deflection voltage V, the distance h between probe and sample can be determined.

The thus determined distance h and the positional relationship between probe and sample can be displayed in real time in subordinate screens on the display apparatus 12, such as those shown in FIG. 8. In this way, the operator can visually recognize the current distance between probe and sample.

While in the above example, the FIB was deflected on either side of the optical axis for improving the distance-recognition performance, it is also possible to recognize the distance by irradiation normal to the sample surface and diagonally on one side. This case is the same as when θ2=0, so that, when the deflected amount at the time of vertical irradiation is d2, $$h = (d1+d2)/\tan \theta 1 \quad (8)$$

When the deflection voltage is V1, we have $$h = (d1+d2) \cdot Lw \cdot Cd/V1 \quad (9)$$

The thus obtained distance between probe and sample can be displayed on the display apparatus 12 as described in Embodiment 1 with reference to FIG. 8, thus allowing the operator to recognize the distance intuitively.

Figure 17:
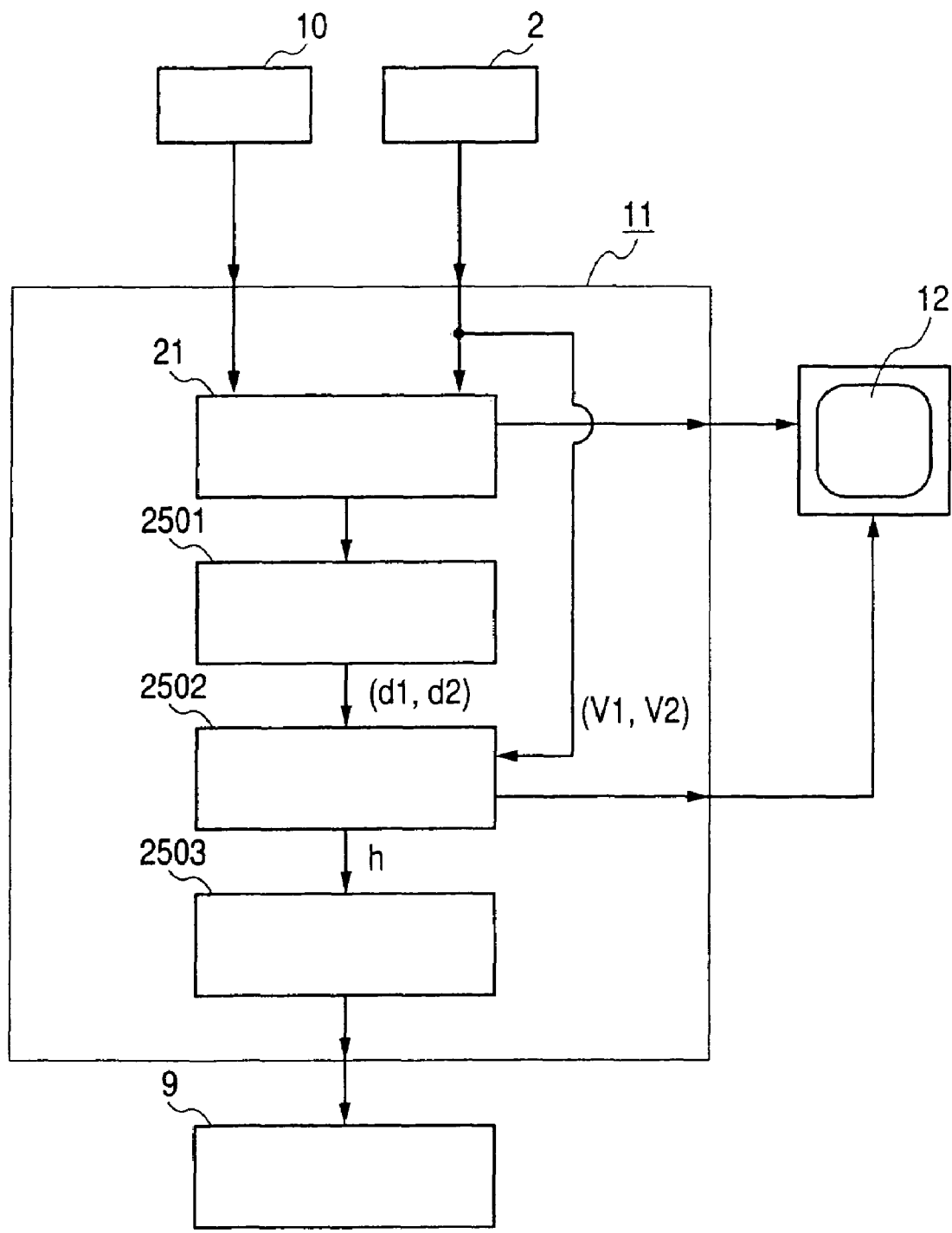
FIG. 17 schematically shows an example of the secondary electron information analyzing apparatus for FIB diagonal irradiation according to the invention.

FIG. 17 is a drawing for the explanation of the signal exchange involving the secondary electron information analyzing apparatus 11 during the diagonal FIB irradiation. An image is generated by the SIM image generating unit 21 based on the deflector scan signal from the ion beam control apparatus 2 and the secondary electron luminance information from the secondary electron detector 10. The image is displayed on the display apparatus 12. Based on this SIM image, displacement amounts d1 and d2 during deflection by V1 and V2 are obtained by a probe displacement amount recognizing unit 2501. Based on V1, V2, d1 and d2, a probe height h is calculated by an interval identifying apparatus 2502. The height h is displayed on the display apparatus 12. An appropriate speed for the probe height h is set by a probe speed selection unit 2503 from which a signal is sent to the probe control apparatus 9.

In the present embodiment, the current distance h between probe and sample can be detected, so that the probe 7 can be prevented from crashing into the sample 4 when the sample base or probe is moving. Further, this embodiment is also effective in removing interference among probes when more than one probe is used.

EMBODIMENT 3

Figure 18:
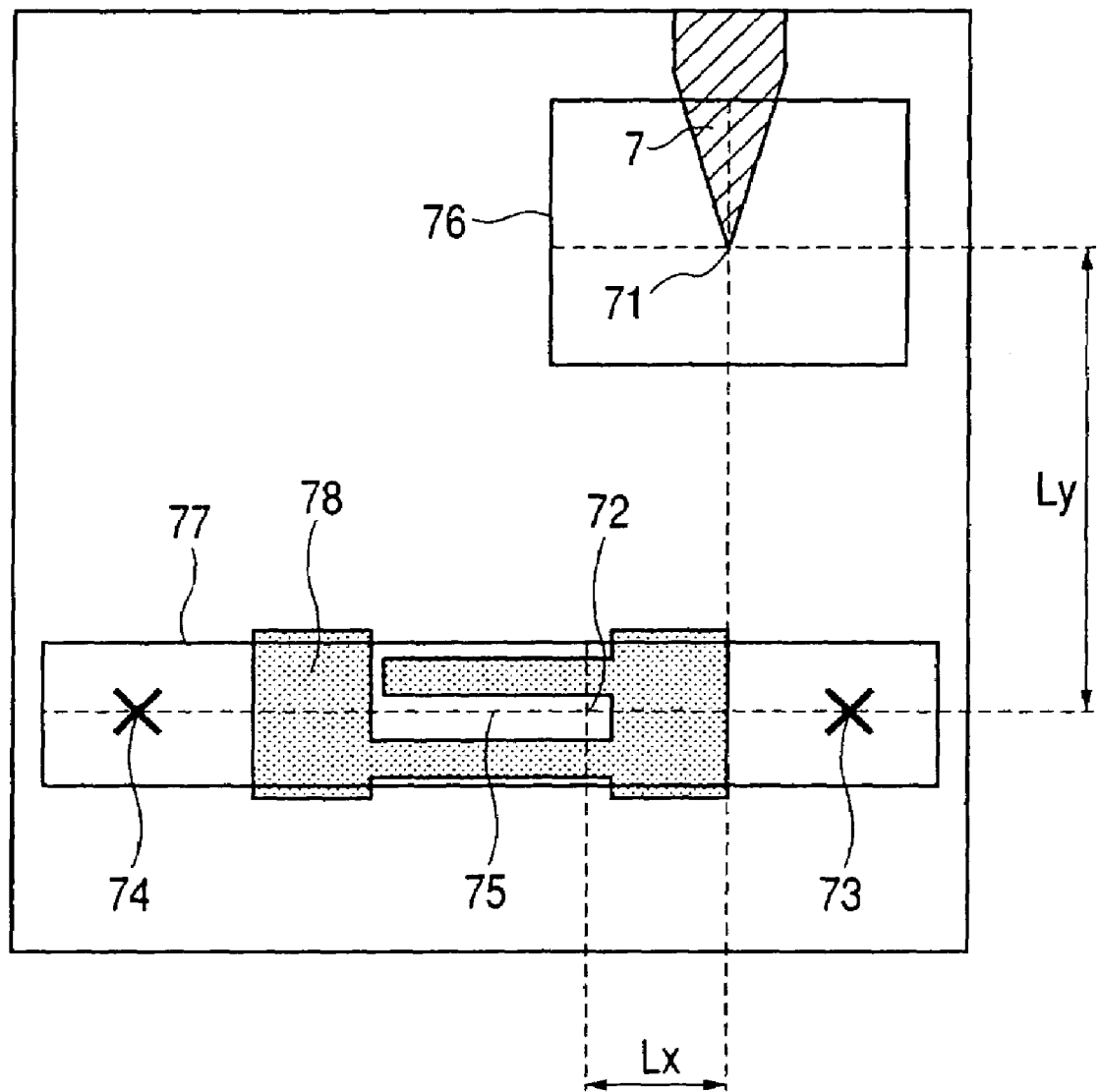
FIG. 18 illustrates a method of automatically acquiring the distance to be traveled by a probe to a position immediately above a target according to the invention.

Referring to FIG. 18, a method of controlling the probe such that the probe tip is transported parallel to the sample surface and brought immediately above a target position of the sample will be described. FIG. 18 shows an SIM image. Numeral 7 designates a probe, 73 and 74 designate marks formed by a FIB, and 78 designates an FIB processed opening. Numeral 75 designates a sample to be removed. The object of the probe operation is to bring the tip 71 of the probe into contact with a probe connection portion 72 of the removed sample 75. A reference image 76 of the probe tip is acquired from the SIM image in advance. Numeral 71 designates the position of the probe tip. Numeral 77 designates an FIB mark reference image for identifying the probe connection portion. By matching the SIM image against the reference images 76 and 77, the position corresponding to the probe tip position in the reference image 76 is identified as the position of the probe tip 71. Likewise, the position corresponding to the position of the probe connection portion in the reference image 77 is identified as the position of the probe connection portion 72. Based on these items of information, displacement amounts Lx and Ly between the current probe tip 71 and the probe connection portion 72 in a plane parallel to the sample surface can be obtained. The probe control apparatus 9 drives the probe driving apparatus 8 by these amounts Lx and Ly, so that the probe tip 71 can be brought immediately above the probe connection portion 72. Thus, by carrying out this control method, the probe tip can be automatically transported to the target position.

EMBODIMENT 4

Hereafter, an embodiment will be described in which the invention is applied to a sample diagnosis apparatus in which the probe is contacted to a sample in an FIB apparatus in order to evaluate the electric characteristics of a sample based on the distribution of secondary electron signal luminance and the current/voltage characteristics as measured by the probe.

Figure 19:
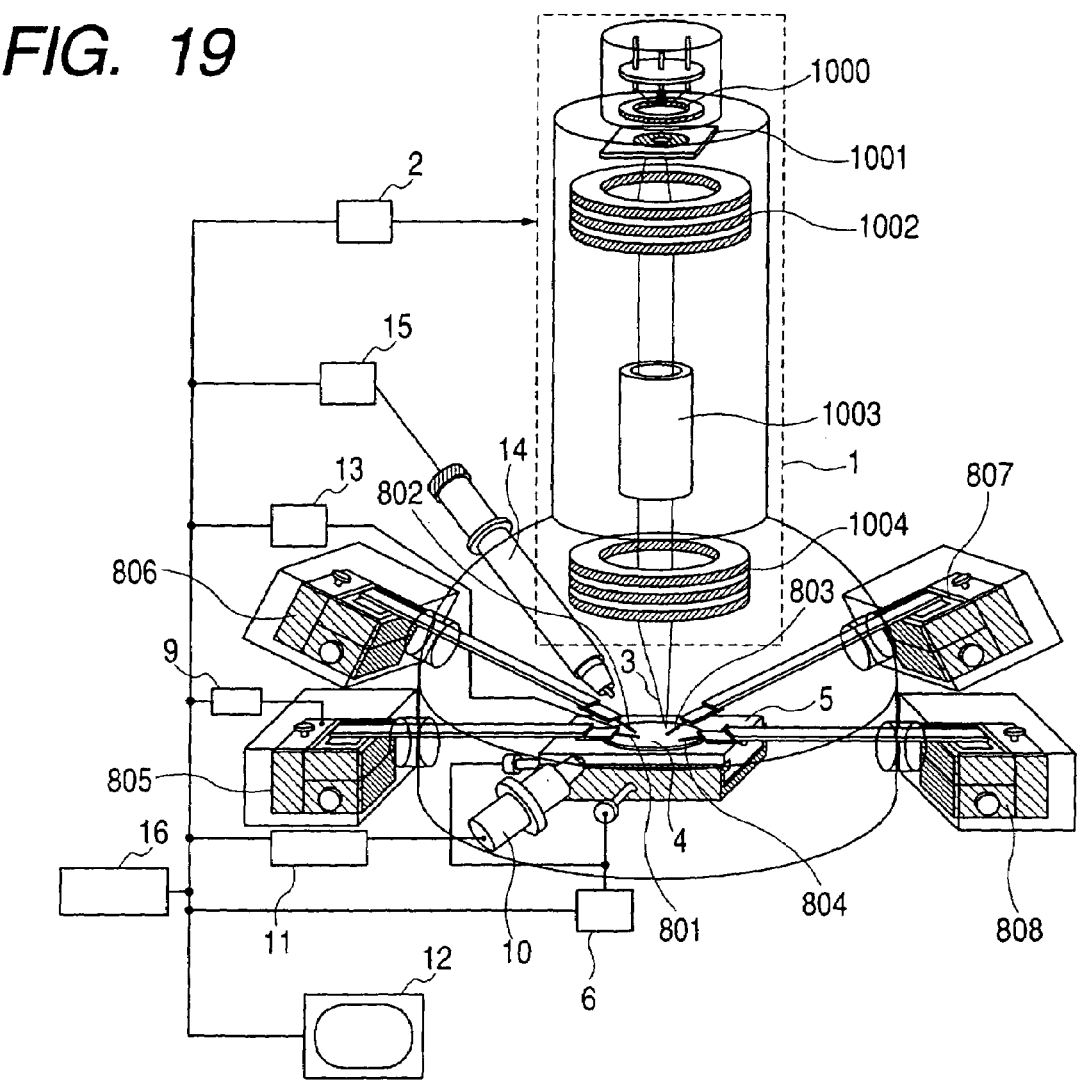
FIG. 19 shows a block diagram of an example of the FIB sample diagnosis apparatus according to the invention.

FIG. 19 shows an example of the constitution of the sample diagnosis apparatus. A sample 4 to be diagnosed, such as a semiconductor wafer or chip, is mounted on a movable sample base 5. The sample 4 is positioned for diagnosis by a sample base control apparatus 6 by which the position of the sample base 5 is controlled. Four probes 801, 802, 803 and 804 (although in the drawing probes 802, 803 and 804 are not shown to be connected to the probe electric control apparatus 13, in fact they are) for supplying voltage to the sample 4 or measuring the resistance, current or the like of the sample, under the control of the probe electric control apparatus 13, are driven by probe driving apparatus 805, 806, 807 and 808 (although in the drawing the apparatus 806, 807, and 808 are not shown to be connected to the probe control apparatus 9, in fact they are), under the control of the probe control apparatus 9.

The surface of the sample 4 and the probe are observed by detecting secondary electrons with a secondary electron detector 10 and displaying an image of the sample and probe on the display apparatus. The electrons are generated as the ion beam 3 from the ion beam optical system 1, under the control of the ion beam control apparatus 2, irradiates the sample surface and probe. The probe control apparatus 9 is controlled by the secondary electron information analyzing apparatus 11, which identifies specific information from the secondary electron information. A deposition gas source 14 is controlled by a deposition gas source control apparatus 15 and supplies tungsten carbonyl gas, for example, above the sample 4. The sample 4 is irradiated with the ion beam 3 so that a tungsten film is formed at the irradiated portion, thereby allowing the wiring to be modified or an electrode pad to be formed.

The ion beam control apparatus 2, deposition gas source control apparatus 15, probe electric control apparatus 13, probe control apparatus 9, secondary electron information analyzing apparatus 11, sample base control apparatus 6, and display apparatus 12 are controlled by a calculation processing unit 16. The calculation processing unit 16 may be realized on a personal computer or a workstation comprising the ion beam control apparatus 2, deposition gas source control apparatus 15, probe electric control apparatus 13, probe control apparatus 9, secondary electron information analyzing apparatus 11, and sample base control apparatus 6.

Figure 20:
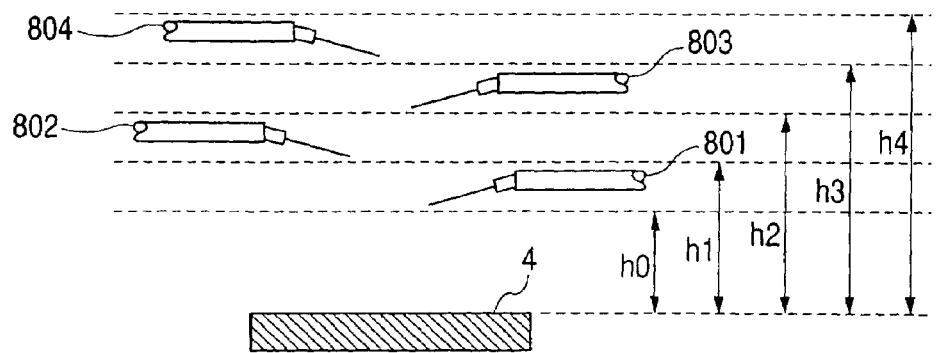
FIG. 20 illustrates a method of transporting a plurality of probes in a plane parallel to a sample in a non-interfering manner according to the invention.

Referring to FIG. 20, a method of transporting a plurality of probes will be described. FIG. 20 shows the positional relationship among a sample 4 and probes 801, 802, 803 and 804 as seen from a direction parallel to the surface of the sample 4. For simplicity, the distance between each probe and the sample will be hereafter referred to as a probe height. In the case where a plurality of probes exist, as in FIG. 20, it is necessary that when one probe moves in a plane ("XY plane") parallel to the sample surface, that probe does not interfere with the other probes. When the probes are in the FIB field of view, this can be ensured by utilizing the probe height monitor used in Embodiment 2. However, when there is a probe outside of the FIB's field of view, it is difficult to recognize possible interference among the probes. In particular, it should be noted that the probe is replaced as an expendable item when the influence which oxidation on the probe surface, for example, has on the measurement of electric characteristics cannot be disregarded anymore. In this light, the height of the probe tip position cannot be accurately recognized solely by means of the absolute coordinates of the probe driving apparatus, and therefore possible interference among the probes cannot be easily recognized.

In the present embodiment, the height of the probe 801 is limited when it is transported in the XY plane even outside of the FIB field of view in order to ensure that the probes do not interfere with each other. Specifically, the probe height is limited within a region of h1 to h0. Similarly, the transportation of probe 802 is limited within a region h2 to h1, probe 803 within a region h3 to h2, and probe 804 within a region h4 to h3. When the probe comes into contact with the sample, the probes are lowered to a region below h0. Namely, each probe is located only within the individually specific height (such as h1 to h0 in the case of the probe 801), or below h0. The heights h0, h1, h2, h3 and h4 are determined by the size of the probe structural portion and the probe attachment tolerance.

By thus setting the specific height of each probe in its intra-XY plane movement, it becomes possible to bring each probe immediately above the target position without interfering with other probes. After the probe is located immediately above the target position, the probe is brought closer to the sample 4 until it contacts the sample in the region of h0. It should be noted, however, that for the intra-XY plane fine movement for the purpose of fine-adjustment of intra-XY plane position, the probe may be moved within the region of h0, for there is no fear of the probe interfering with other probes there. In other words, for fine-adjustment purposes, the probe does not have to be brought up to the individually assigned height for transportation. Thus, this probe control method can remove interference among the probes when more than one probe is simultaneously moved, so that the probes can be transported in a short time.

Figure 21:
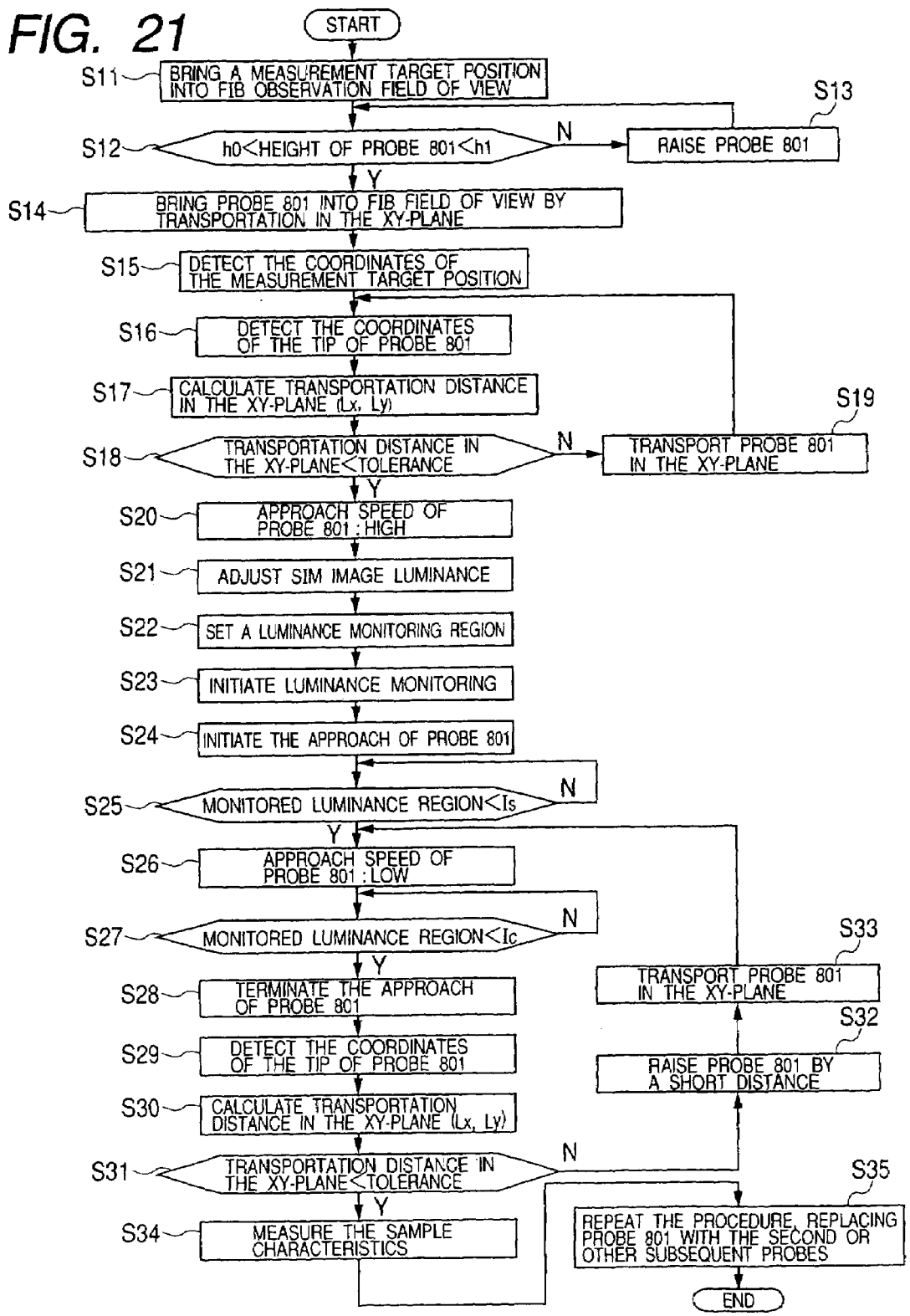
FIG. 21 shows a flowchart of the procedure for realizing probe contact according to the invention.

FIG. 21 shows a flowchart of the contact flow based on the above method. First, the sample base is transported into the FIB observation field of view at the target position for measurement (S11). Then, the probe 801 is introduced into the FIB field of view through the following flow by the intra-XY plane non-interfering transportation method for the probe (see FIG. 20). Initially, it is determined whether h0<(height of probe 801)<h1 (S12). If outside this range (N), the probe 801 is in the region below h0, so the probe 801 is raised (S13). Herein the direction in which the probe approaches the sample is referred to as descent, and the opposite, separating direction is referred to as ascent. As the probe 801 enters the region h0 to h1 (Y), the probe 801 is introduced into the FIB field of view by transporting it in the XY plane (S14).

Next, the probe 801 is transported immediately above the target position by the method of obtaining the coordinates of the probe tip position and contact target position based on the reference images, as described by referring to FIG. 18. This is done through the following flow. First, the target position coordinates ($Xs1$, $Ys1$) are obtained by detecting the coordinates of the target position by image matching (S15). The probe tip coordinates ($Xp1$, $Yp1$) are then obtained by detecting the coordinates of the tip of the probe 801 by image matching (S16). Based on the difference between these two sets of coordinates, the transportation distance ($Lx$, $Ly$)=($Xs1-Xp1$, $Ys1-Yp1$) in the XY plane is calculated (S17). Then, it is determined whether the transportation distance in the XY plane is less than the tolerance amounts ($Lx<Lxe$, $Ly<Lye$) (tolerance amounts ($Lxe$, $Lye$) are set in advance) (S18). If the result of this determination is (N), the probe 801 is transported in the XY plane ($Lx$, $Ly$) (S19). In this way, the probe tip position is brought to within the tolerance range immediately above the target position.

The approach speed of the probe 801 is then set at a high speed (such as 1 mm/s) (S20). The luminance of the SIM image is adjusted so that the sample surface can be observed on the display apparatus 12 and that at the same time the probe luminance does not saturate (S21). The luminance monitoring region is then set near the probe 801, as shown in FIG. 2 (S22), and luminance monitoring is initiated (S23). As the probe 801 approaches the sample (S24), it is determined whether the monitor region luminance I is less than a preset threshold luminance Is (S25). If the result of determination is (N), the approach of the probe continues at the high speed and, when the monitored region luminance I falls below Is (Y), the approach speed of the probe is switched to a slow speed (such as 0.5 μm/s) (S26). Then, it is determined whether the monitored region luminance I is greater than a preset threshold luminance Ic (S27). If the result of determination is (N), the approach of the probe continues and, when the monitored region luminance I rises above Ic (Y) and contact is detected, the approach of the probe 801 is terminated (S28).

Then the coordinates of the probe tip ($Xp1$, $Yp1$) are again obtained by detecting the coordinates of the probe tip by image matching (S29). Based on the difference between these coordinates and the coordinates of the target position ($Xs1$, $Ys1$) obtained in the step of detecting the coordinates of the target position (S15), the transportation distance ($Lx$, $Ly$)=($Xs1-Xp1$, $Ys1-Yp1$) in the XY plane is calculated (S30). Next, it is determined whether the transportation distance in the XY plane is less than the tolerance ($Lx<Lxe$, $Ly<Lye$) (S31). If the result is (N), the probe 801 is raised by a short distance (S32), transported in the XY plane ($Lx$, $Ly$) (S33), and the approach of the probe 801 is repeated at the slow speed (S26). Eventually, when the condition of the transportation distance in the XY plane being less than the tolerance ($Lx<Lxe$, $Ly<Lye$) is satisfied (Y), the contact of the probe tip to the target position is completed. Thereafter, the sample characteristics are measured based on SIM contrast and probe current, for example, in the probe electric control circuit 13 (S34). When a plurality of probes are used, the probe 801 is replaced with the second or other subsequent probes and the entire measurement process is repeated (S35).

The above flow can be conducted entirely automatically once the probe tip reference image and the contact target position reference image are set and the luminance monitored position is designated in advance. Thus the probe can be automatically brought into contact with the sample and the burden on the operator can be reduced.

Figure 22:
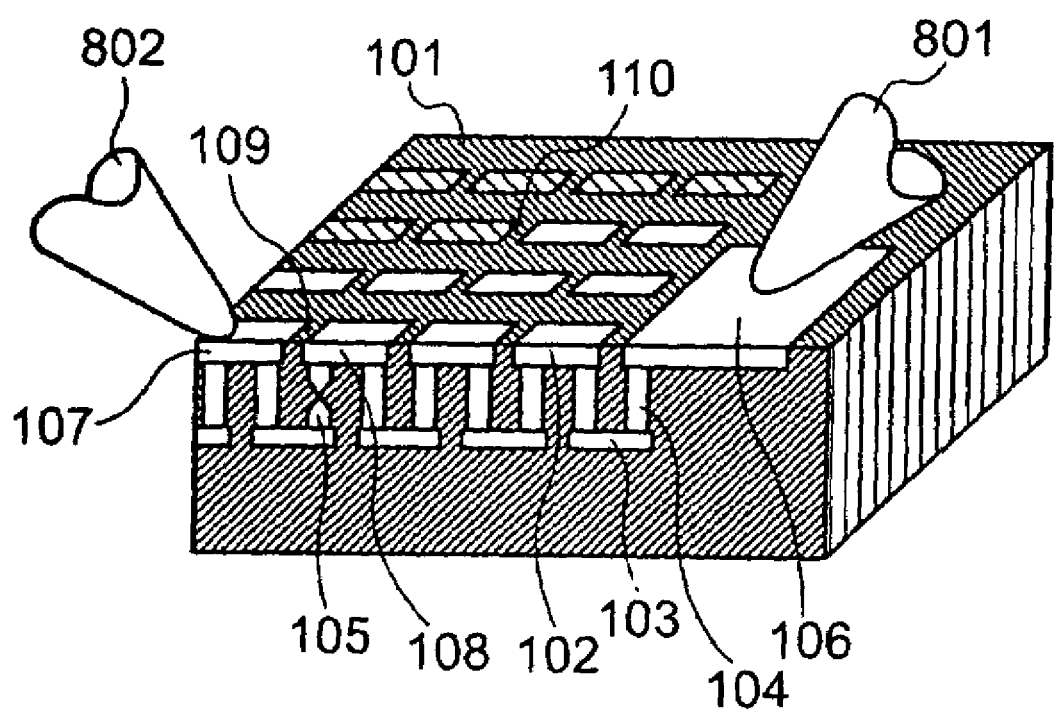
FIG. 22 illustrates an example of the manner in which wiring breakage is detected by the FIB sample diagnosis apparatus according to the invention.

Referring now to FIG. 22, an example in which a wire breakage portion of a device wiring on the surface of a sample is identified by the apparatus according to the invention will be described. In the drawing, numeral 101 designates a measuring device, numeral 102 a metal wiring on the sample surface, and numeral 103 a metal wiring inside the sample. The metal wirings 102 and 103 are connected by a connection plug 104 in a chain structure, as shown. As shown, there is breakage in a connection plug 105.

The probe 801 is brought into contact with an electrode pad 106 on this device in the manner described in the above flow. Since a wiring region 107 down from the breakage portion is electrically floating, it is charged by FIB irradiation and appears dark in a secondary electron image. This is due to the following reasons. In the present embodiment, positive gallium ions are used in the FIB irradiation. As the floating portion is irradiated with positive ions in the FIB, positive charges are injected. At the same time, secondary electrons are emitted, so that the floating portion is further positively charged. When the floating portion is positively charged to some extent, the emitted secondary electrons are pulled by the potential of the floating electrode. This reduces the efficiency with which the secondary electrons are acquired by the secondary electron detector, resulting in a reduction in the secondary electron signal luminance. On the other hand, electric charges are discharged through the probe from the wiring regions 106 to 108 with which the probe is electrically connected, so that there is no reduction in luminance in the secondary electron signal from these regions. Thus, a wire breakage portion 109 can be identified based on the difference in secondary electron luminance before and after the broken connection plug 105.

If any subsequent breakage portions are to be identified, the probe 802 is brought into contact with the metal wiring 107 located downstream of the above breakage portion according to the same flow. This way, a subsequent wire breakage portion 110 can be identified based on the difference in secondary electron luminance. In this case, by applying a voltage between the probes 801 and 802 and thereby detecting the current flowing therebetween, the resistance of the wire breakage portion can be measured.

By arranging the system so that the probes 801, 802, 803 and 804 can be switched by the probe electric control apparatus 13 for each specific role, such as the measurement of current or application of voltage, any desired type of measurement can be conducted by any of the probes no matter which electrode a particular probe is in contact with. This arrangement allows greater freedom of movement for the probes than is the case when assigning a specific role, such as measurement of current, application of voltage or grounding, to each of the probes beforehand, making diagnosis easier.

Figure 23:
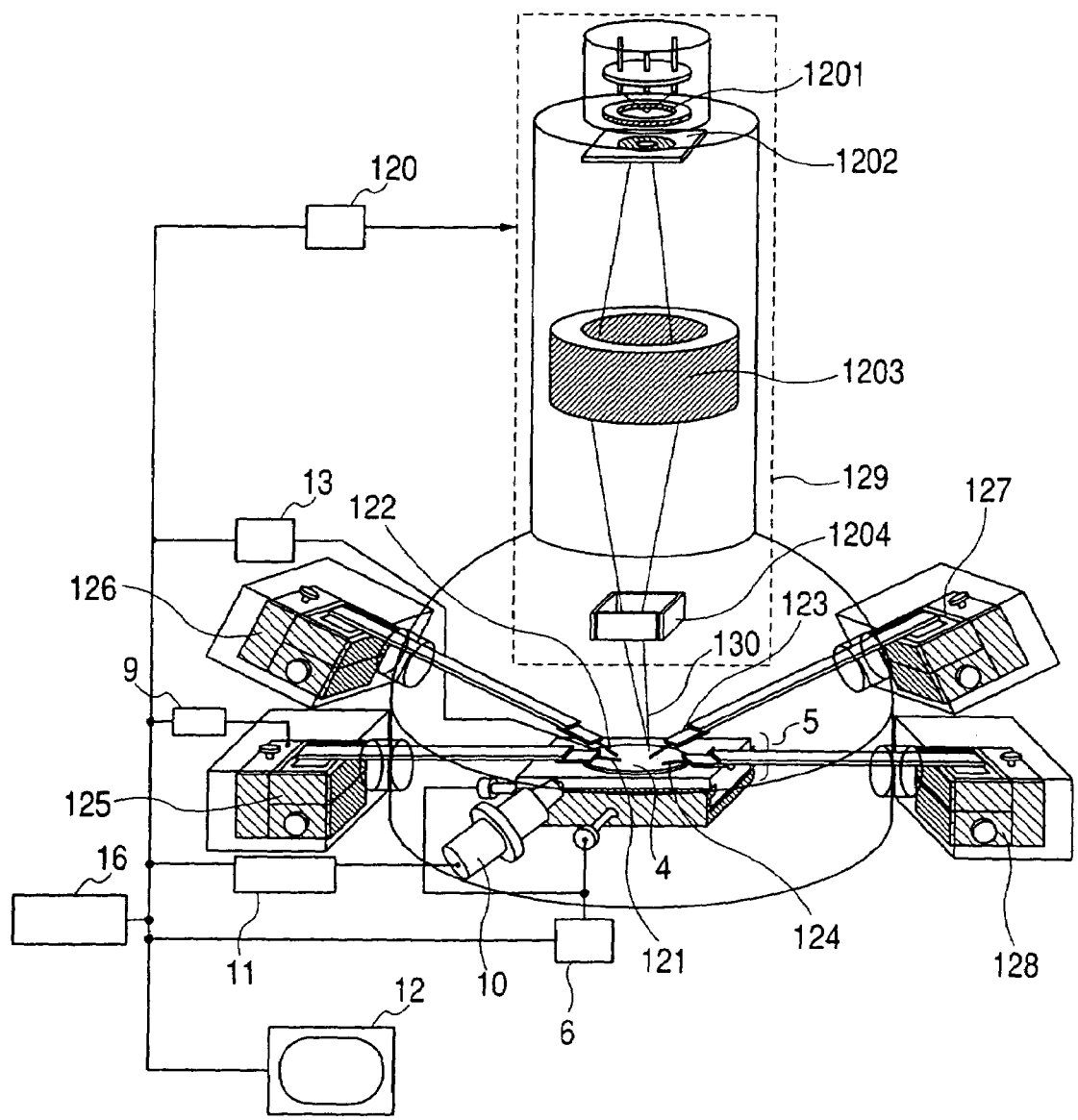
FIG. 23 shows a block diagram of an example of the electron beam sample diagnosis apparatus according to the invention.

In place of a FIB, an electron beam optical system 129 that is under the control of an electron beam control apparatus 120 can be used. FIG. 23 shows an example of the sample diagnosis apparatus using the electron beam optical system 129. A sample 4 to be diagnosed, such as a semiconductor chip or wafer, is mounted on a movable sample base 5. The sample is positioned for diagnosis by a sample base control apparatus 6 by which the position of the sample base 5 is controlled. Four probes 121, 122, 123 and 124 (although in the drawing the probes 122, 123 and 124 are not shown to be connected to the probe electric control apparatus 13, in fact they are) for supplying voltage to the sample 4 and measuring the resistance, current or the like of the sample, under the control of the probe electric control apparatus 13, are driven by probe driving apparatus 125, 126, 127 and 128 (although in the drawing the apparatus 126, 127 and 128 are not shown to be connected to the probe control apparatus 9, in fact they are), under the control of the probe control apparatus 9.

The sample 4 is irradiated with an electron beam emitted by an electron source 1201 via an electron beam optical system 129 under the control of the electron beam control apparatus 120. The electron beam optical system 129 comprises a beam limiting aperture 1202 for limiting the electron beam emitted by the electron source 1201 to a predetermined size, a focusing lens 1203 for focusing the electron beam, and a deflector 1204 for deflecting the beam to a predetermined position on the sample. Secondary electrons generated when the sample or probe is irradiated with the electron beam 130 from the electron beam optical system 129 are detected by the secondary electron detector 10. The output of the detector is fed to the display apparatus 12 as a luminance signal in synchronism with the scan signal applied to the deflector 1204. As a result, an image of the sample surface and images of the probes 121, 122, 123 and 124 are displayed on the display apparatus 12. During this process, the probe control apparatus 9 is controlled by the secondary electron information analyzing apparatus 11 identifying specific information in the secondary electron information. The electron beam control apparatus 120, probe electric control apparatus 13, probe control apparatus 9, secondary electron information analyzing apparatus 11, sample base control apparatus 6, and display apparatus 12 are controlled by the calculation processing unit 16. The calculation processing unit 16 may be realized in a personal computer or a workstation comprising the electron beam control apparatus 120, probe electric control apparatus 13, probe control apparatus 9, secondary electron information analyzing apparatus 11, and sample base control apparatus 6. The sample image and the probe image may also be observed by detecting, with a reflected electron detector, electrons reflected by the sample or probe and feeding a reflected electron detection signal to the display apparatus 12.

However, as opposed to that which is the case with FIB irradiation, since both the primary electron beam 130 irradiated onto the sample and the emitted secondary electrons are negatively charged, the charged state on the sample surface varies depending on the secondary electron emission efficiency, which is the average number of secondary electrons emitted per incident electron. Namely, when the secondary electron emission efficiency is smaller than 1, the sample surface is negatively charged, while when it is larger than 1, the sample surface is positively charged. For this reason, in order to identify the wire breakage portion based on the state of charging as with the FIB sample diagnosis apparatus, the irradiation must be performed under conditions where the secondary electron emission efficiency has a value other than 1.

The apparatus according to this example has the advantage that, since the irradiation beam 130 for observation is made up of electrons, the sample is not damaged even if it is irradiated for a longtime, in contrast to that which is the case with FIB. Thus, the apparatus is useful when the probes 121, 122, 123, and 124 are to be contacted to a microscopic region, such as a single electron transistor, with high accuracy by the probe driving apparatus 125, 126, 127 and 128.

EMBODIMENT 5

Figure 24:
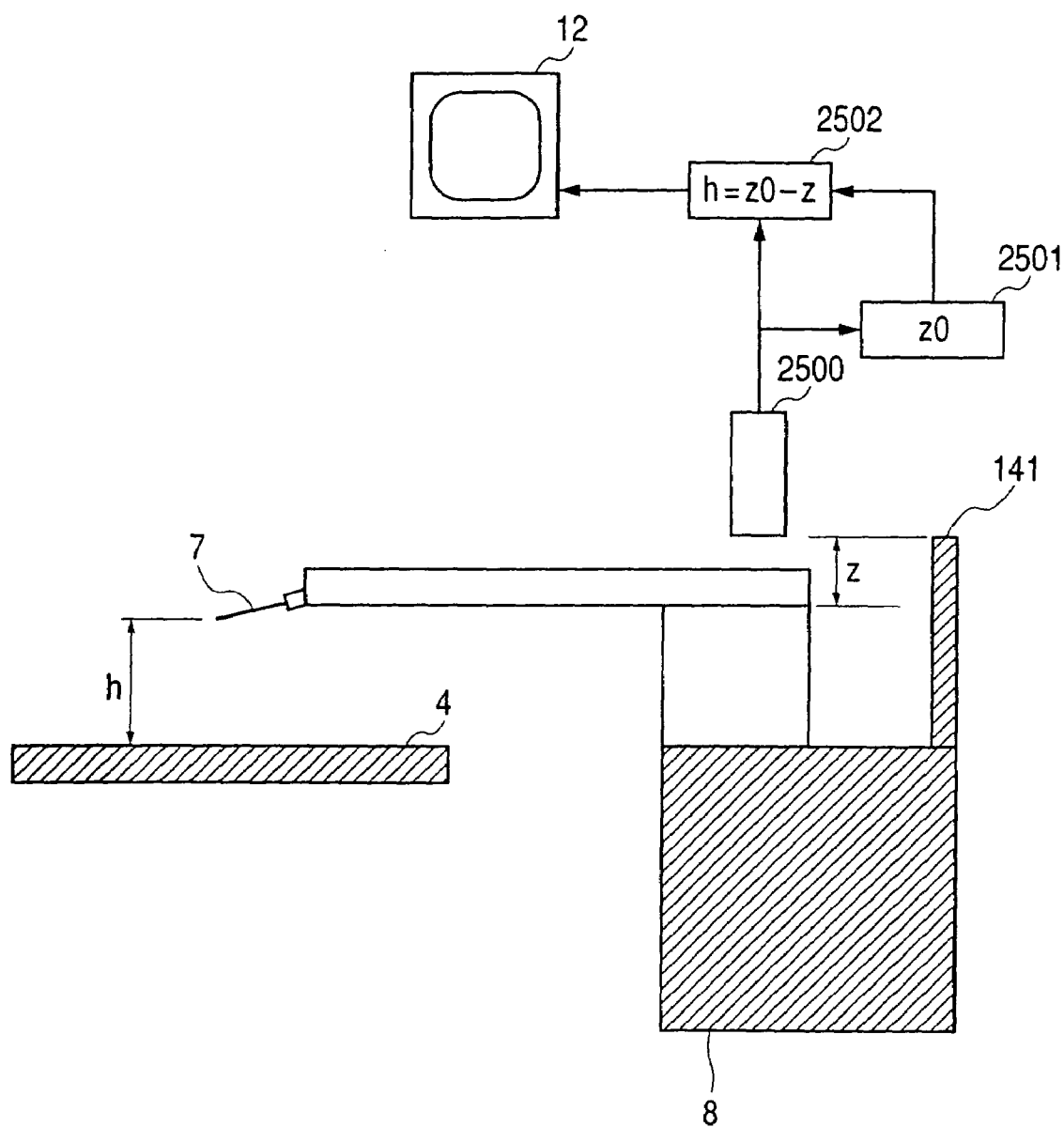
FIG. 24 illustrates a technique for determining the distance between probe and sample by an open-loop control according to the invention.
Figure 25:
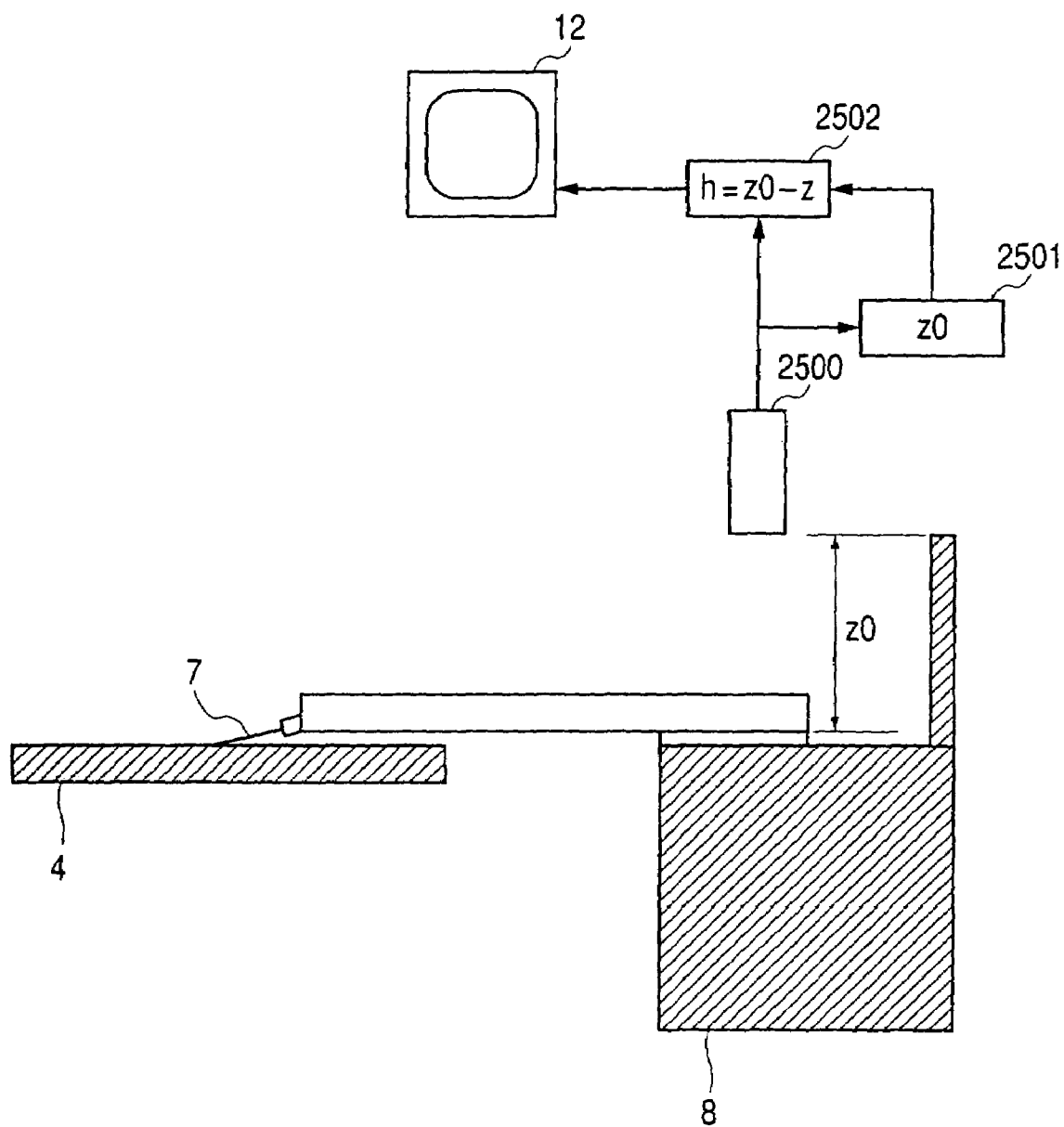
FIG. 25 illustrates a preliminary contact according to the invention.
Figure 26:
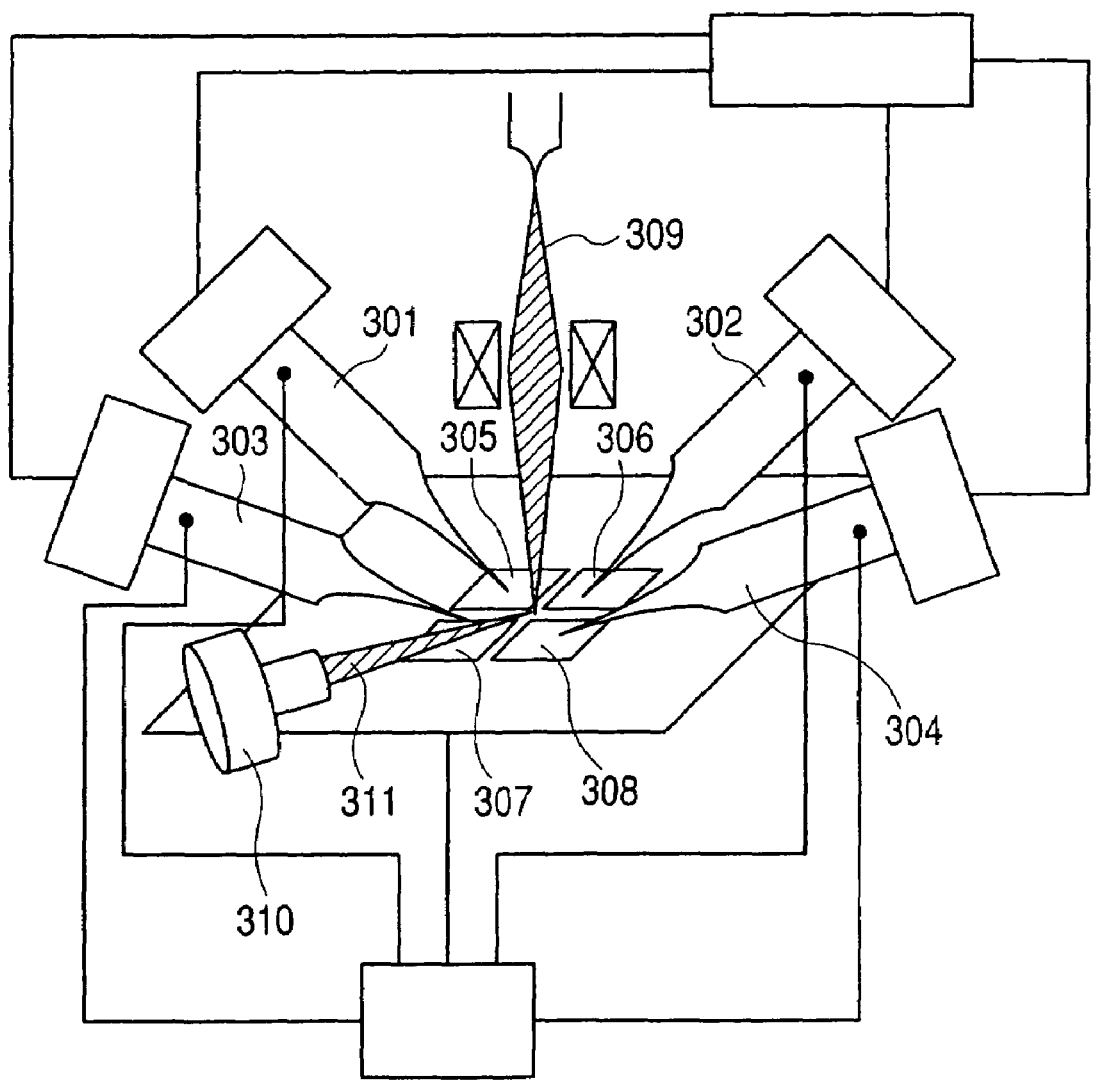
FIG. 26 schematically shows a conventional sample diagnosis apparatus.

Referring to FIGS. 24 and 25, a probe control technique in which the probe tip coordinates are recorded by preliminary contact of the probe will be described. The overall configuration of the apparatus is similar to the one shown in FIG. 1, so FIGS. 24 and 25 show only those portions related to the probe driving apparatus 8.

FIG. 24 shows the height relationship between the sample 4 and the probe 7 as seen from a direction parallel to the sample surface. Numeral 141 designates a point-of-origin sensor indicating the position of the point of origin (z=0) of the probe driving apparatus. In the state as shown in FIG. 24, while the probe driving apparatus 8 possesses probe-position coordinates information z along direction z as measured by a height sensor 2500, it does not know the relationship between this information z and the distance h between the probe tip and sample. In order to clarify the relationship between z and h, the probe 7 is brought into contact with the sample 4 in advance, as shown in FIG. 25, before the probe is actually used for the removal of a removed sample or is contacted with a measuring electrode. This contact is confirmed by detecting a change in secondary electron signal luminance, as described above or, if a conduction path is available, by detecting a contact current. The z coordinate z0 of the probe driving apparatus upon the probe 7 contacting the sample 4 is recorded by a probe reference coordinates recording apparatus 2501.

Once this confirmation is made, when the probe z-coordinate is z, the height h of the probe can be known at all times by a probe height calculator 2502 according to the following equation:

$$h = z0 - z$$

In the present case, the probe 7 approaches the surface of the sample 4 in a positive direction along the z-axis. Because the probe height can be known, the probe can be brought into contact with the sample accurately in a short time without causing damage to the sample or probe. For example, when the probe is actually used in the sample preparation or diagnosis apparatus described in the above embodiments for removing a sample or contacting with a measuring electrode, the probe 7 can approach the sample surface at a high speed up to such z (=z0-10 μm) that h=10 μm and thereafter, the approach speed can be switched to a slower speed. In this case, however, since the probe 7 is controlled in an open-loop system which includes mechanical errors such as backrush, a leeway must be provided in the z-axis tolerance range for those errors. This embodiment is particularly suitable for a sample diagnosis apparatus in which the same probe is contacted a number of times.

INDUSTRIAL APPLICABILITY

The present invention enables the probe to be driven automatically without causing damage to the probe or sample. The invention therefore allows the operator to prepare a sample or electrically diagnose a device sample in an efficient manner while putting less of a burden on the operator.

What is claimed is:

1. A probe apparatus comprising:
   a sample base to mount a sample;
   a charged particle beam optical system to irradiate a charged particle beam to the sample;
   a detector to detect secondary electrons or reflected electrons which generate from the sample;
   a probe to contact with the sample surface;
   a probe control apparatus to control movement of the probe;
   an analyzing apparatus to determine a height between a tip of the probe and the sample surface, and to analyze a signal from the detector; and
   a display apparatus to display an image of the signal,
   wherein the display apparatus displays the information of the height between the tip of the probe and the sample surface based on the analysis result.

2. A probe apparatus according to claim 1, wherein the analyzing apparatus determines a relation of the height between the tip of the probe and the sample surface based on a change in luminance of the image.

3. A probe apparatus according to claim 1, wherein the display apparatus displays a numerical value of the height which is determined by the analyzing apparatus.

4. A probe apparatus according to claim 1, wherein the analyzing apparatus calculates a probe drive speed according to the height.

5. A probe apparatus according to claim 4, further comprising:
   a probe control apparatus to control a movement of the probe based on the calculation result.

6. A probe apparatus according to claim 4, further comprising:
   a probe operating apparatus which makes the probe apparatus approach the sample manually based on the calculation result.

7. A probe apparatus according to claim 1, further comprising:
   a probe control apparatus to control a movement of the probe based on the information of the height.

8. A probe apparatus according to claim 6, further comprising:
   an input device to operate the probe.

9. A probe apparatus according to claim 8, wherein the input device includes a push button, joystick or mouse.

10. A probe apparatus according to claim 7, further comprising:
    an input device to operate the probe.

11. A probe apparatus according to claim 10, wherein the input device includes a push button, joystick or mouse.

12. A probe apparatus according to claim 1, further comprising:
    a buzzer or an indicator to caution when the height approach a preset value.

13. A probe apparatus according to claim 5, wherein the probe control apparatus makes the probe drive speed slow down when the height approaches a predetermined value.

14. A probe apparatus according to claim 4, further comprising;
    a probe control apparatus to control a movement of the probe;
    a probe operating apparatus which makes the probe apparatus the sample manually; and
    a changeover switch to select the analyzing apparatus or the probe operating apparatus based on the calculation result.

15. A probe apparatus according to claim 1, further comprising:
  a probe control apparatus to control a movement of the probe;
  a probe operating apparatus which makes the probe approach the sample manually; and
  a changeover switch to select the analyzing apparatus or the probe operating apparatus based on the information of the height.

16. A probe apparatus comprising:
  a sample base to mount a sample;
  a charged particle beam optical system to irradiate a charged particle beam to the sample;
  a detector to detect secondary electrons or reflected electrons which generate from the sample;
  a probe to contact with the sample surface;
  a probe control apparatus to control movement of the probe;
  an analyzing apparatus to determine a distance between the probe and the sample surface, and to analyze signal from the detector; and
  a display apparatus to display an image of the signal,
  wherein the display apparatus displays the information of the distance between the probe and the sample surface based on the analysis result.

* * * * *

UNITED STATES PATENT AND TRADEMARK OFFICE
CERTIFICATE OF CORRECTION

| | |
|---|---|
| PATENT NO. | : 7,301,146 B2 |
| APPLICATION NO. | : 11/201222 |
| DATED | : November 27, 2007 |
| INVENTOR(S) | : Satoshi Tomimatsu et al. |

Page 1 of 1

It is certified that error appears in the above-identified patent and that said Letters Patent is hereby corrected as shown below:

Title Page, Insert Items:

-- (86) PCT No.: PCT/JP01/04875
       §371 (c)(1), (2), (4) Date: Nov. 29, 2002
  (87) PCT Pub. No. WO02/08774
       PCT Pub. Date: Jan 31, 2002

(30) Foreign Application Priority Data:

Jul 24, 2000   (JP) ............... 2000-222882 --

Signed and Sealed this

Third Day of June, 2008

JON W. DUDAS
*Director of the United States Patent and Trademark Office*